United States Patent [19]
Pathak et al.

[11] Patent Number: 5,849,035
[45] Date of Patent: Dec. 15, 1998

[54] METHODS FOR INTRALUMINAL PHOTOTHERMOFORMING

[75] Inventors: Chandrashekhar P. Pathak, Waltham; Amarpreet S. Sawhney, Lexington, both of Mass.; Jeffrey A. Hubbell, San Marino, Calif.; Stephen J. Herman, Andover, Mass.; Laurence A. Roth, Windham, N.H.; Patrick K. Campbell, Georgetown; Kevin M. Berrigan, Woburn, both of Mass.; Peter K. Jarrett, Southbury, Conn.; Arthur J. Coury, Boston, Mass.

[73] Assignee: Focal, Inc., Lexington, Mass.

[21] Appl. No.: 448,572

[22] PCT Filed: Apr. 28, 1994

[86] PCT No.: PCT/US94/04824

§ 371 Date: Oct. 30, 1995

§ 102(e) Date: Oct. 30, 1995

[87] PCT Pub. No.: WO94/24962

PCT Pub. Date: Nov. 10, 1994

Related U.S. Application Data

[63] Continuation-in-part of Ser. No. 54,385, Apr. 28, 1993, abandoned.

[51] Int. Cl.⁶ .......................................................... A61F 2/06
[52] U.S. Cl. ................................ 623/1; 606/108; 606/194
[58] Field of Search ..................................... 623/1; 604/49, 604/96, 100; 128/898–9; 606/192, 194, 7, 13–16, 108

[56] References Cited

U.S. PATENT DOCUMENTS 3,847,771  11/1974  McGinniss .
3,878,075   4/1975  McGinniss .

(List continued on next page.)

FOREIGN PATENT DOCUMENTS

| 0 355 200 | 2/1990 | European Pat. Off. . |
|---|---|---|
| 402467 | 12/1990 | European Pat. Off. . |
| 0 466 178 | 9/1991 | European Pat. Off. . |
| 0 540 290 | 5/1993 | European Pat. Off. . |
| WO 90/01969 | 8/1990 | WIPO . |
| WO 91/12846 | 5/1991 | WIPO . |
| WO 95/08289 | 9/1994 | WIPO . |

OTHER PUBLICATIONS

Mehmet et al., "Tissue Soldering by use of Indocyanine Green Dye–Enhanced Fibrinogen with the Near Infrared Diode Laser". J. Vascular Surgery, 11:5 (May, 1990) Applicants' Informal Translation of Portions of EP 0466178.

Poppas, D.P. et al., "Chromophore Enhanced Laser Welding of Canine Ureters in Vitro Using A Human Protein Solder: A Preliminary Step for Laparoscopic Tissue Welding", The Journal of Urology, vol. 150, pp. 1052–1055, Sep. 1993.

(List continued on next page.)

*Primary Examiner*—Mark Bockelman
*Attorney, Agent, or Firm*—Wolf, Greenfield & Sacks, P.C.

[57] ABSTRACT

A method and apparatus for molding polymeric structures in vivo is disclosed. The structures comprise polymers that may be heated to their molding temperature by absorption of visible or near-visible wavelengths of light. By providing a light source that produces radiation of the wavelength absorbed by the polymeric material, the material may be selectively heated and shaped in vivo without a corresponding heating of adjacent tissues or fluids to unacceptable levels. The apparatus comprises a catheter having a shaping element positioned near its distal end. An emitter provided with light from at least one optical fiber is positioned within the shaping element. The emitter serves to provide a moldable polymeric article positioned on the shaping element with a substantially uniform light field, thereby allowing the article to be heated and molded at a desired treatment site in a body lumen.

64 Claims, 7 Drawing Sheets

U.S. PATENT DOCUMENTS

| | | |
|---|---|---|
| 3,915,824 | 10/1975 | McGinniss . |
| 4,023,559 | 5/1977 | Gaskell . |
| 4,233,493 | 11/1980 | Nath . |
| 4,248,214 | 2/1981 | Hannah et al. . |
| 4,336,809 | 6/1982 | Clark . |
| 4,444,927 | 4/1984 | Borysko . |
| 4,445,892 | 5/1984 | Hussein et al. . |
| 4,575,181 | 3/1986 | Ishikawa . |
| 4,575,373 | 3/1986 | Johnson . |
| 4,669,465 | 6/1987 | Moore et al. . |
| 4,754,752 | 7/1988 | Ginsburg et al. . |
| 4,799,479 | 1/1989 | Spears . |
| 4,801,477 | 1/1989 | Fudim . |
| 4,846,165 | 7/1989 | Hare et al. . |
| 4,878,492 | 11/1989 | Sinofsky . |
| 4,892,098 | 1/1990 | Sauer . |
| 4,955,377 | 9/1990 | Lennox et al. . |
| 5,009,655 | 4/1991 | Daignault . |
| 5,053,033 | 10/1991 | Clarke . |
| 5,066,231 | 11/1991 | Oxman . |
| 5,085,629 | 2/1992 | Goldberg . |
| 5,092,841 | 3/1992 | Spears ............................................ 623/1 |
| 5,100,429 | 3/1992 | Sinofsky et al. ............................. 623/1 |
| 5,126,141 | 6/1992 | Henry . |
| 5,145,945 | 9/1992 | Tang . |
| 5,147,385 | 9/1992 | Beck . |
| 5,156,613 | 10/1992 | Sawyer . |
| 5,156,620 | 10/1992 | Pigott . |
| 5,163,952 | 11/1992 | Froix . |
| 5,178,618 | 1/1993 | Kandarpa . |
| 5,185,408 | 2/1993 | Tang . |
| 5,196,005 | 3/1993 | Doiron . |
| 5,199,951 | 4/1993 | Spears . |
| 5,209,748 | 5/1993 | Daikuzono . |
| 5,209,776 | 5/1993 | Bass . |
| 5,213,115 | 5/1993 | Zytkovicz . |
| 5,213,580 | 5/1993 | Slepian . |
| 5,226,430 | 7/1993 | Spears . |
| 5,292,362 | 3/1994 | Bass . |
| 5,300,020 | 4/1994 | L'Esperance . |
| 5,312,395 | 5/1994 | Tan . |
| 5,334,191 | 8/1994 | Poppas et al. . |
| 5,454,794 | 10/1995 | Narciso et al. . |

OTHER PUBLICATIONS

Choma, T.J., M.D. et al., "$CO_2$ Laser Urethroplasty in the Rabbit: A Preclinical Model", Lasers in Surgery and Medicine, vol. 12, pp. 639–644, 1992.

Klioze, S.D. et al., "Development and Initital Application of a Real Time Thermal Control System for Laser Tissue Welding", The Journal of Urology, vol. 152, pp. 744–748, Aug. 1994.

Poppas, D.P. et al., "Laser Welding in Urethral Surgery: Improved Results with a Protein Solder", The Journal of Urology, vol. 139, Feb., 1988, pp. 415–417.

Poppas, D.P. et al., "Patch Graft Urethroplasty Using Dye Enhanced Laser Tissue Welding with a Human Protein Solder: A Preclinical Canine Model", The Journal of Urology, vol. 150, pp. 648–650, Aug. 1993.

Poppas, D.P. et al., "Preparation of Human Albumin Solder for Laser Tissue Welding", Lasers in Surgery and Medicine, vol. 13, pp. 577–580, 1993.

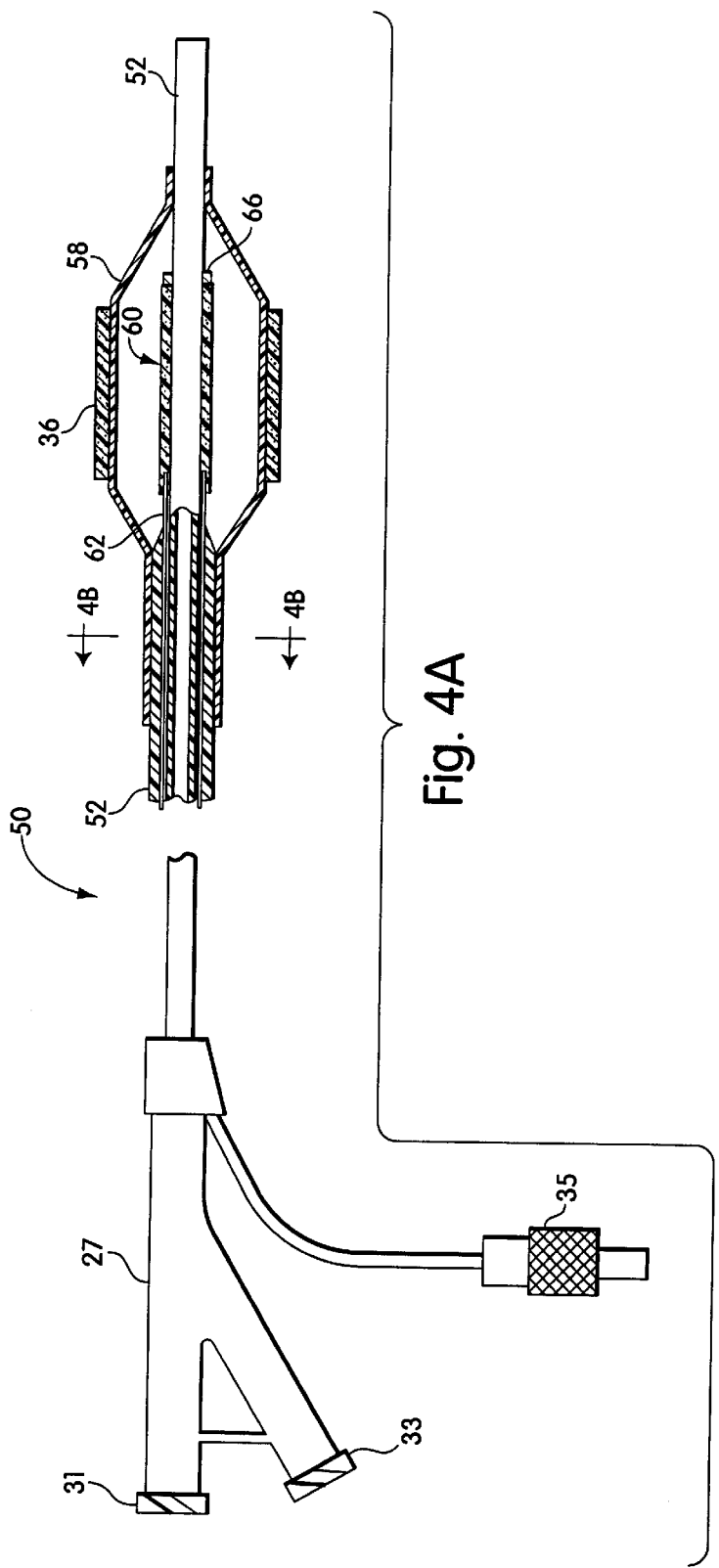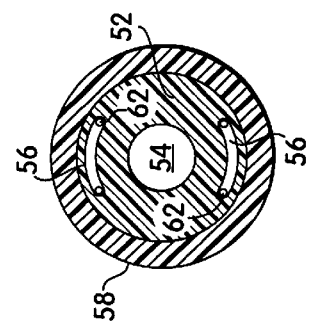
Fig. 4A
Fig. 4B

METHODS FOR INTRALUMINAL PHOTOTHERMOFORMING

RELATED APPLICATION DATA

This application is a national application (35 U.S.C. §371) of international application Ser. No. PCT/US94/04824, filed Apr. 28, 1994, which is a continuation-in-part of U.S. application Ser. No. 08/054,385, filed Apr. 28, 1993 (abandoned).

FIELD OF THE INVENTION

This invention pertains to devices for intraluminal implantation of polymeric materials in a human or animal patient and methods for delivering such materials.

BACKGROUND OF THE INVENTION

The application of polymeric materials to body tissues of human or animal patients is becoming increasingly important in medicine. Among the proposed uses of such materials are the alteration of tissue; the creation or preservation of lumens, channels or reservoirs for the passage or collection of fluids; the creation of matrices for the growth of tissue; the control of undesirable tissue growth; the delivery of therapeutic agents to a tissue surface; the ability to join a tissue surface to another tissue or an artificial implant; the ability to isolate or protect tissue or lesions to enable or mediate healing; and the ability to mediate the rate of substances or energy passing into, out of, or through tissue.

Although it has been recognized that the use of polymeric materials in vivo may offer significant therapeutic effects, to date such applications have met many limitations. For example, the methods for applying such polymers to tissue surfaces often require the use of pressure, heat or electrical energy exceeding limits of tolerability at the tissue site. Likewise various chemical effects associated with such polymers have been found to be physiologically unacceptable.

Numerous methods for reshaping polymeric materials in vivo are known in the prior art. In particular, U.S. Pat. No. 5,213,580 and International Publication WO 90/01969, both to Slepian et al., the entire disclosures of which are incorporated herein by reference, describe methods in which polymers having melting points slightly above physiological temperatures are implanted into a patient and in which such polymers are melted via contact with heated fluids and shaped using mechanical force provided by a balloon catheter. Unfortunately, many of the methods known in the art suffer from the need to use energy levels beyond those which are physiologically tolerable, or from the inability to sufficiently control the shape change and/or temperature of the polymeric material.

Typically, the primary limitation in prior art methods for the delivery of energy to an implanted device is the inability to direct the energy specifically to the device, while minimizing energy delivery to body tissue. For example, it is known in the prior art that polymeric devices such as stents may be delivered to specific locations in vivo using a balloon catheter. Such stents may be heated at the site by filling the balloon with a heated fluid. In that method, heat is conducted from the fluid in the balloon, through the balloon material, and into the stent. Since conduction is a relatively slow process and the balloon has a relative large thermal mass, energy is transferred not only to the stent, but also to the surrounding body tissues and fluids. The result is that undesired amounts of heat are transferred into the surrounding body tissues and fluids.

Accordingly, a need exists for apparatus for implanting polymeric materials in vivo that avoids the problems associated with the prior art. A need also exists for methods for delivering and reshaping materials in vivo which allow a physician to safely and easily introduce the material into a patient, configure the material as desired, and deposit the material at a desired location for at least a therapeutically desirable period of time. A further need exists for materials and methods for reshaping such materials in vivo that offer the ability to reshape the materials while minimizing the amount of energy that is transferred to surrounding tissues and physiological fluids.

SUMMARY OF THE INVENTION

The present invention pertains to apparatus and methods for the delivery of polymeric material in vivo, and more particularly to the implantation of polymeric material into tissue lumens of human or animal patients, More particularly the invention relates to methods for photothermoforming a polymeric article in vivo, that is, modifying the shape of a polymeric article in vivo by using light to selectively heat the article to a temperature at which it is fluent, molding the article into a desired conformation, and allowing the article to become non-fluent in the desired conformation. Material from which the article is made is selected such that it is moldable at a temperature at which substantial damage to adjacent or proximate tissue does not occur.

Heating is achieved by irradiating, or illuminating the article with light of a wavelength or within a wavelength range at which the polymeric material readily absorbs, or at which adjacent tissue or body fluids do not significantly absorb. According to one aspect of the invention, the article is irradiated at a wavelength or within a wavelength range at which the polymeric material readily absorbs and at which adjacent tissue or fluids do not significantly absorb.

This is achieved by providing polymeric material that relatively strongly absorbs the radiation provided, or by loading the polymeric material with a chromophore that readily absorbs the radiation. It is preferred that the light used to thermoform the polymer be of a wavelength that is not readily absorbed by body tissues or fluids, thereby minimizing the amount of light absorbed by, and heat generated in, the tissue or fluid in the region of the thermoforming. According to one aspect of the invention visible or near-infrared light is provided locally to the polymeric material by an optical tip assembly on a delivery device.

The resulting shaped article provides a therapeutic benefit by acting, in one embodiment, as a stent to maintain patency through a blood vessel. Numerous other therapeutic shapes are contemplated as well.

According to one embodiment, the polymeric material has a chromophore such as a dye or pigment compounded therein. The chromophore is selected, in conjunction with a particular light source, to absorb light that is produced by the light source. The absorbed light is converted to thermal energy which acts to heat the polymer. According to one aspect of the invention, the chromophore is thermochromic. As an alternative to compounding the polymer with a chromophore, polymers that naturally absorb the wavelength spectrum of the light produced by the source may be used. The natural absorption spectrum of the material may result from the polymer in its native state, or alternatively, by the incorporation of one or more chromophores into the polymeric backbone or side-chains. In each case, however, it is necessary that the polymer satisfies other selection criteria such as biocompatibility and moldability.

By selecting a chromophore, or polymeric material, having maximum absorption characteristics at or near a particular wavelength or spectral range, in conjunction with a light source that emits at or near the particular wavelength or spectral range, the polymer is provided with the ability to be efficiently heated via light absorption. In this way, selective heating of the polymer with minimal heating of surrounding body tissues and fluids may be achieved.

Broadly, the apparatus comprises a catheter having a shaping element positioned near its distal end. The polymeric material is positioned adjacent or near the shaping element, illuminated by light delivered by the catheter and thus heated to render it fluent, and molded by the shaping element into contact with a tissue lumen.

In one embodiment, the apparatus comprises a balloon dilatation catheter having an associated optical tip assembly. The polymeric material is positioned on the balloon, preferably in the form of a tube or sleeve which surrounds the balloon. The optical tip assembly serves to direct light to the polymeric material. The light may be provided from an external source. Upon absorption of the light, the polymeric material is heated to a temperature at which it becomes moldable. Inflation of the balloon causes the moldable polymeric material to expand outwardly, thereby pressing the polymer into contact with the tissue lumen. Alternatively, in cases in which the polymeric material can be reconfigured prior to molding (i.e., the polymeric material comprises a rolled sheet or a tube having axial pleats), the material is reconfigured using the balloon and then heated to mold it into conformance with an adjacent tissue surface.

According to another embodiment, the apparatus further includes a retractable sheath which is designed to encapsulate the polymeric material on the balloon as the material is guided to a treatment location in vivo. Once positioned, the sheath is retracted to expose the material and to allow the material to be heated and molded as described above. The sheath may include a tapered distal tip, formed of a flexible polymer, which expands radially over the balloon and polymeric material as the sheath is withdrawn over those structures. As an alternative, the tip may include at least one longitudinal slit which allows radial expansion of the tip.

BRIEF DESCRIPTION OF THE DRAWINGS

FIGS. 4a and 4b illustrate a second embodiment of a laser balloon catheter suitable for delivery of a polymeric material;

DETAILED DESCRIPTION OF THE INVENTION

Figure 1:
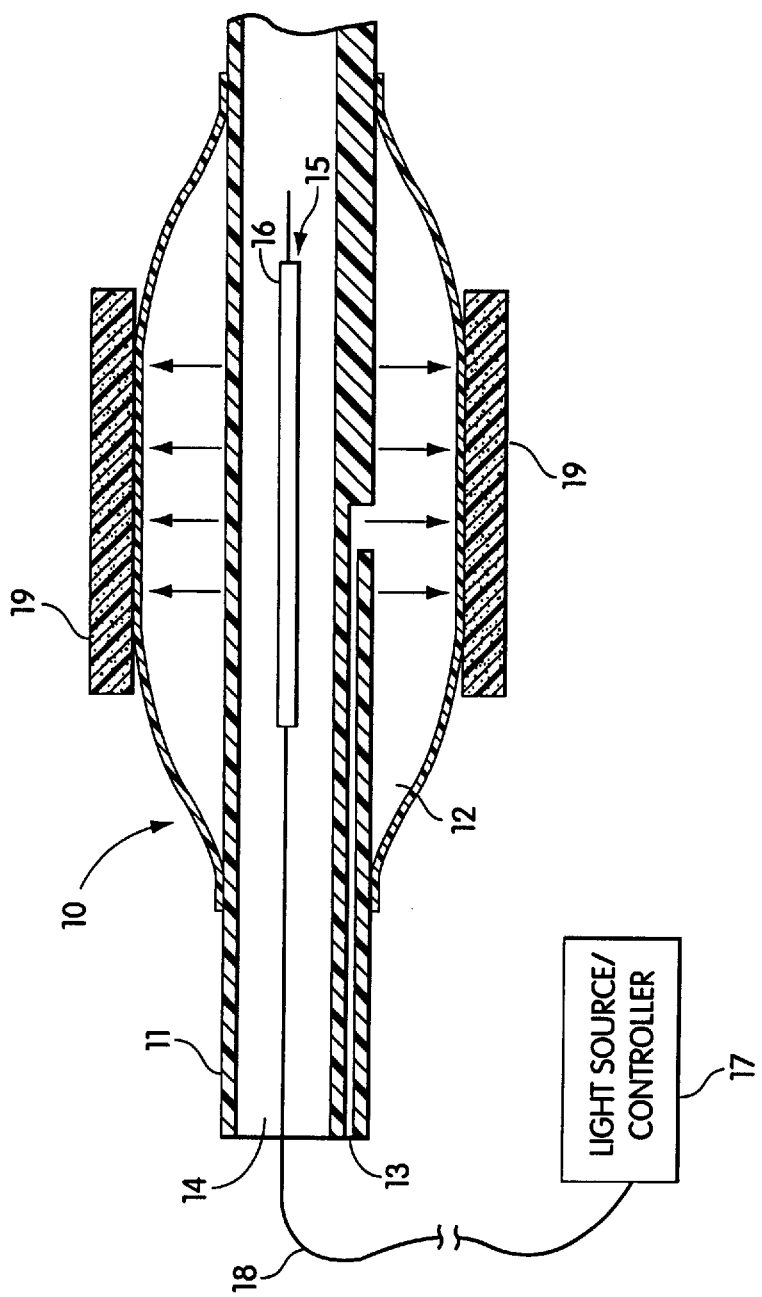
FIG. 1 illustrates one embodiment of a laser balloon catheter suitable for delivery of a polymeric material.

The ability to selectively heat an implanted polymeric material using light in the visible or near-visible spectrum can be achieved using a light source which produces a wavelength spectrum that is not readily absorbed by body tissue. Light from the source is used to heat a polymeric material that is at least partially absorptive of the light in the spectral range. Even if only a portion of the light (e.g., 50%) is absorbed by the polymer, transmitted light will not be readily absorbed by the surrounding tissue and will have a minimal heating effect on that tissue. In this case, light which is not absorbed by the polymer is absorbed by a relatively large area of tissue as it penetrates beyond the polymer. As such, resultant heating occurs throughout a much larger volume of tissue. Since the temperature rise in the tissue is a function of energy absorbed within a unit volume of tissue, localized heating is significantly lower as compared to the heating caused by wavelengths that are readily absorbed, i.e., by a smaller volume of tissue. The requirement for wavelengths which have low tissue absorption characteristics is necessary only to the extent that excess heating of the tissue does not occur or is undesirable at the particular treatment location.

Alternatively, it is possible to use light having a spectrum that is absorbed by body tissues and fluids provided that the polymeric material is highly absorptive of light in the spectral range. In this case, the polymer will absorb substantially all of the light, thereby minimizing the amount that is transferred to the body tissue and minimizing the heating effect of that light on tissue.

The polymeric materials of the present invention must satisfy various criteria, including molding temperature, crystallinity, absorption characteristics, bioerodability, physical strength, biocompatibility and light transmission and absorption characteristics. Each of these are discussed below.

Molding Temperature

The material must become either moldable or molten at a temperature that is not significantly injurious to tissue or surrounding physiological fluids if maintained at that temperature for the amount of time required to implant and shape the material. Additionally, the material must become moldable at a temperature above about 40 degrees C. That temperature has been selected as being a temperature that is greater than body temperatures associated with hyperthermia or fever (approximately 38–40 degrees C.). The requirement of the minimum molding temperature is to prevent the material from spontaneously softening or melting in response to elevated, physiologically occurring body temperatures.

As used herein, the term "molding temperature" is used to describe a minimum melting temperature, $T_m$, or a glass transition temperature, $T_g$, at which the polymer may be plastically deformed using physiologically acceptable forces. Likewise, the melting or glass transition temperature are must be below that at which significant mechanical or thermal damage to body tissues occurs. The term "thermoforming" is used to describe the process wherein a polymeric article is heated to at least its molding temperature and then reshaped by external or internal forces.

Crystallinity and Physical Strength

It is preferred that the material have a substantially crystalline or semi-crystalline structure so that when heated to its melting temperature, it will undergo a rapid transition to a viscous fluid that will flow readily, yet remain cohesive, when subjected to molding forces associated with thermoforming. As an alternative, the material may be glassy or have a glassy component. In that case, if heated sufficiently above its glass transition temperature, the material will also flow readily and remain cohesive when subjected to molding forces.

The materials useful in the invention are termed "fluent" when in their moldable state. The actual viscosity of the fluent material that allows the material to be molded without significant mechanical disruption of the tissue depends upon the particular tissue and the method by which the material is molded. In general, it is preferred that the material be such that, once heated to its molding temperature, (i.e., rendered fluent), the material may be shaped or formed using a physiologically acceptable amount of force. Likewise, it is preferred that the molding temperature be low enough to prevent significant thermal damage during the molding process. The ability to be molded using a minimum amount of force reduces the possibility of tissue injury potentially occurring as a result of misuse or structural failure of the polymeric material or the force-supplying component.

Determination of an acceptable amount of force and thermal load depends upon at least a) the viscosity of the material in its moldable state, b) the length and/or thickness of the material, c) the geometric configuration of the material, and d) the temperature at which the material becomes sufficiently fluent. Additionally, forces and thermal loads that may be physiologically acceptable on one type of tissue may not be acceptable on another. For example, physiologically acceptable forces and temperatures within bone tissue may far exceed the amount of force and heat that is physiologically acceptable on a blood vessel or other soft tissue. Thus, the physical characteristics of both the polymeric material and the tissue site must be considered in determining maximum physiologically acceptable forces and temperatures for molding the polymer.

It is preferred that the selected polymeric material be such that the amount of thermal energy needed to heat the material to its molding point can be transferred within a practical amount of time to thereby minimize the length of time required for the surgical procedure and to minimize the amount of heat conducted out of the material and into the tissue.

In one embodiment, the material is intended to provide mechanical support to tissue structures. In that embodiment, the material itself, and the ultimate therapeutic shape of the material, must provide a structure having sufficient mechanical strength to withstand forces exerted upon the shaped material during its functional lifetime in vivo. This requirement is especially significant when using materials that are expected to be biodegradeable after their mechanically functional lifetime. Alternatively, the material need not be intended for structural support. Rather, the material may be used as a protective layer, a barrier layer, as an adhesive, or as a carrier of therapeutic agents. In that case, the material must be selected so that its function is not impaired either by biodegradation during its functional lifetime in vivo or by the process used to shape the material during implantation. The ability to provide varied degrees of mechanical support can be achieved by selecting differing polymeric materials or by altering the molecular weight distribution of materials comprising more than one polymer. In general, materials having higher molecular weights will provide a higher modulus and greater support than those materials having a lower molecular weight. Additionally, the material must be selected such that the heating and reformation of the material do not degrade or otherwise alter the release characteristics of the material toward any therapeutic agents that may be incorporated into the material.

In some applications it is preferred that the material not completely cover, but only partially cover an area of tissue to be supported or otherwise addressed by the material. For example, the material may be applied to support a portion of a tissue lumen, rather than the entire lumen. The physical form may be varied to suit the final application. While relatively thin solid films or sheets are preferred for many applications, fenestrated or microporous sheets may also be used. Spun webs, with or without melt-bonding or calendaring, may also be of use. The material can include predefined perforations or apertures once transformed from a delivery configuration to its therapeutic configuration. If the device is intended to be delivered in the form of a hollow cylinder, the cylinder may be provided with a plurality of perforations which open or remain open once the cylinder has been expanded to a larger, therapeutic configuration. If the material is used as a support structure for an artery, the perforations may allow increased axial flexibility to facilitate delivery and reduce tissue erosion during and after implementation, improved perfusion of side branch vessels by decreasing the likelihood of obstruction of such vessels, and increased ingrowth of tissue for anchoring and encapsulation of the material.

Absorption Characteristics

The polymeric material should preferably absorb light within a wavelength range that is not readily absorbed by tissue, blood elements, physiological fluids, or water. Although wavelengths in the spectral range of about 250–1300 nm may be used, wavelengths in the range of about 300–1000 nm are preferred, and wavelengths in the range of about 500–850 are especially preferred. In the case in which a chromophore such as a dye or pigment is incorporated into the polymeric material, the material itself must be sufficiently transparent to allow the light to reach and be absorbed by the dye or pigment.

For both the bioerodable and non-bioerodable polymers, chromophores and light sources suitable for use in the invention may be selected from dye or pigment materials and lasers corresponding to those materials including, but not limited to, the following:

| Wavelength (nm)/laser | Dye/Maximum Absorption |
|---|---|
| 457 Argon Ion | Acramine Yellow (420 nm) |
| 488 Argon Ion | Acridine Orange (489 nm), Fluorenscein (491 nm) |
| 514 Argon Ion | Eosin Y (514 nm) |
| 676 Argon/Krypton | Methylene Blue (661 nm) |
| 647 Krypton | Jenner stain (651 nm), |
| 676 | Methylene Blue (661 nm) |
| 694 Ruby | Prussian blue (694 nm), |
| 780 Semiconductor | Copper Phthalocyanine |
| 780 | (795 nm in sulfuric acid), |
| 810 | Indocyanine Green (775 nm) |
| 820 | |
| 830 | |
| 850 | |
| 870 | |
| 532 Neodymium:YAG (frequency X2) | Ethyl Eosin (532 nm in ethanol); Erythrosin B (525 nm); Eosin Y (514 nm) |
| 355 Neodymium:YAG (frequency X3) | Acridine (358 nm) |
| 266, Nodymium:YAG (frequency X4) | Prussian blue (260 nm), |
| All | Carbon black |

The selection of light source and chromophore is not intended to be limited solely to those specified above.

Rather, any combination that yields sufficient heating to render the polymeric material fluent may be used.

Any of a variety of methods known in the art of polymer processing may be used to form the polymeric material into its predeployment configuration and, if necessary, to compound chromophores into the material. Among the polymer processing methods contemplated are solvent casting, injection molding, extrusion, solvent extraction and compression molding.

The heating method of the present invention may be contrasted with conductive heating methods which use a heating element, as such techniques tend to require a greater thermal load and to heat more slowly, thereby having the potential to transfer significant amounts of heat to the surrounding body tissue or fluids, As noted previously however, absorption of light allows the polymeric article to be heated while transferring a minimum of energy to the surrounding tissue and fluids. This is achieved by selecting either a wavelength spectrum that is not readily absorbed by body tissue, a polymeric composition that absorbs substantially all incident energy in the wavelength spectrum, or a combination of these characteristics.

In one embodiment, the upper limit of the polymer temperature can be controlled using a dye which substantially stops absorbing optical energy once it reaches a certain temperature. Such so-called "thermochromic" dyes are commercially available from Clark R&D Limited of Arlington Heights, Ill. Thermochromic dyes exhibit a constant absorption below a lower critical temperature $T_L$. Between $T_L$ and an upper critical temperature $T_U$ the absorption decreases from a constant value to nearly zero. Thermochromic dyes are further characterized generally in that the change of absorption with temperature is fully reversible. The incorporation of thermochromic dyes into polymeric materials allows constant absorption of energy when the polymer is cool with a decreasing energy absorption as the polymer is heated. It is expected that the polymer temperature will reach a steady state at some point between $T_L$ and $T_U$ resulting from a balance between the energy absorbed by heat input from the light source and the energy lost by heat output to the surrounding tissue.

For example, Type 47 thermochromic dye available from Clark R&D absorbs, at room temperature, light in the wavelength spectrum between about 600 and about 850 nm. The dye has a $T_L$ of 44 degrees C. and a $T_U$ of 58 degrees C. If this dye is compounded into a polymer having a melting temperature ($T_M$) that falls between $T_L$ and $T_U$, the resulting polymeric material will absorb light in the 600–850 nm spectrum and begin to heat. Once the polymeric material is heated to a temperature above $T_L$, the absorption of the dye will decrease, thereby decreasing the rate of polymeric heating and preventing the polymeric material from achieving a temperature that may be harmful to it, and adjacent body tissue or surrounding body fluids. Once the temperature of the polymeric material reaches $T_M$, the polymer melts, allowing it to pave an adjacent tissue surface. However, since the temperature rise will decrease and reach a steady state level where the energy input (reduced due to decreased dye absorption) equals the energy output (mediated by thermal boundary conditions) an upper thermal limit is achieved. Thermochromism thus is essentially a feedback mechanism for obtaining uniform heating of the entire article despite possible non-uniformity of illumination. The hottest regions of the polymer will absorb less light, allowing other areas of the device to "catch up" in temperature during the heating stage. Thermochromic dyes can render instrumentation to measure temperature of the polymeric material unnecessary.

In addition, the use of thermochromic dyes may offer advantages if the emitter is eccentrically located inside a shaping element such as a balloon. Since power density from the emitter is approximately related to the inverse or the inverse square of the distance between the emitter and the polymeric material, the power density would be much higher for a portion of polymeric material close to the emitter than for a portion of the material that is further away. When using conventional dyes, the result can be a non-uniform temperature around the shaping element, resulting in one portion of the polymeric material being much warmer than another. However, if a thermochromic dye is incorporated into the polymeric material, the material that is located closer to the emitter would rapidly reach its maximum temperature and level off, while material on a further portion of the polymeric material would reach the same maximum temperature, although more slowly. The result is that ultimately the entire polymeric article would reach a uniform temperature. Likewise, different thermal boundary conditions at the surface onto which the polymeric article is being applied could also, if conventional dyes are used, cause the polymeric article to become warmer in some sections than in others. This difference can also be reduced if thermochromic dyes are employed.

In still another embodiment, a thermochromic dye can be used in combination with a conventional dye. Thus, rather than reaching a steady state condition in which the thermal input is equal to the thermal output as a result of near zero dye absorption, a combination of thermochromic and conventional dyes would cause the heating to slow as the absorption of the thermochromic dye decreases. However, even if the thermochromic dye reaches a state of zero absorption, the heating level would continue to increase as a result of the presence of the conventional dye until a steady state is reached. By varying the relative proportions of conventional dye to thermochromic dye, the heating of the polymeric article can be tailored to a specific application.

Bioerodability

Although not intended to be limited as such, in one embodiment, the polymeric materials of the invention preferably are bioerodable. The term "bioerodable" as used herein is intended to encompass many modes of material removal, such as enzymatic and non-enzymatic hydrolysis, oxidation, and enzymatically-assisted oxidation. It is thus intended to include degradation, bioresorption and dissolution.

If the polymeric materials are to be bioerodable, they should be selected on the basis of their degradation characteristics to provide a sufficient functional lifespan for the particular application. In the case of arterial applications, a functional lifespan of 3–6 months is believed to be sufficient. In other therapeutic applications, (i.e., trachial, urinary, bronchial, bone lumens and the like) shorter or longer periods may be appropriate.

Suitable bioerodable polymeric materials include, but are not limited to, polymers, copolymers and blends of:

A. Polyanhydrides (especially those made using melt condensation, solution polymerization, or with the use of coupling agents, aromatic acids, aliphatic diacids, amino acids (such as aspartic acid and glutamic acid), and the copolymers thereof).

B. Copolymers of epoxy terminated polymers with acid anhydrides.

C. Polyorthoesters

D. Homo- and copolymers of α-hydroxy acids including lactic acid, glycolic acid, ε-caprolactone, γ-butyrolactone, and δ-valerolactone.

E. Homo- and copolymers of α-hydroxy alkanoates.

F. Polyphosphazenes.

G. Polyoxyalkylenes, where alkene is 1 to 4 carbons, as homopolymers and copolymers including graft copolymers.

H. poly(amino acids), including pseudo poly(amino acids).

I. Polydioxanones

J. Copolymers of polyethylene glycol with any of the above.

Suitable non-bioerodable polymeric materials include, but are not limited to, polymers, copolymers and blends of:

K. Polyalkenes (such as polypropylenes)

L. Polymethacrylates

M. Polyacrylates

N. Polyesters

O. Polyamides (such as nylons)

P. Polysaccharides (such as dextran)

In accordance with the invention, it is contemplated to blend or copolymerize materials to obtain desired properties in terms of melting point, strength, and biocompatibility.

Polycaprolactone homopolymers and copolymers are highly suitable bioabsorbable polymers for use in accordance with the invention, particularly for the prevention of abrupt closure or restenosis in a blood vessel, or for the creation of radially expanded lumens through a blood vessel, trachea, urethra or other tissue lumen. Such materials possess adequate strength in their solid form to structurally support soft tissue lumens. Additionally, once positioned and molded to a desired shape in a body lumen or hollow organ, the physical structure of such materials is sufficiently non-variable, in the period prior to its bioerosion, to maintain constant dimensions in the molded article. Thus, the materials provide structures such as stents that, although flexible, do not significantly deform in the period between implantation and degradation. Such dimensionally stable, shaped articles eliminate risks associated with known helical or spring metal stents which may have a tendency to continue to expand once positioned in a lumen, thereby exerting continuous or increasing pressures on the lumen wall. Furthermore, polymeric stents of the type described conform, when fluent, to lumen irregularities. In the case of blood vessels, such conformity tends to avoid causing blood flow discontinuities which can contribute to thrombus formation. Stents formed of structural metallic or polymeric filaments do not closely conform to the lumen, thereby creating areas of blood stagnation and turbulence.

Polycaprolactones have a crystalline melting point of approximately 60 degrees C. and can be deployed in vivo using the methods described herein. Additionally, such materials in their fluent state are well adapted for mechanical deformation to various degrees and into various configurations.

Polycaprolactone homopolymers and copolymers bioabsorb at rates that are advantageous in many applications in which biodegradability is desired. These materials can be designed to resorb as soon as three months after implantation or as long as three years after implantation. For example, polycaprolactone copolymerized with lactic or glycolic acids may resorb over a 3—9 month period, whereas polycaprolactone homopolymers may resorb over a 2–3 year period. The ultimate degradation product of polycaprolactones is a non-toxic, 6-hydroxy hexanoic acid having a pH close to neutral.

In contrast to the polycaprolactones, other bioabsorbable polymers such as polygycolides and polylactides melt at temperatures on the order of approximately 180 degrees C., a temperature well above that tolerable by human tissue. However, these materials have glass transition temperatures of approximately 45 degrees C., thus they are moldable at physiologically tolerable temperatures and potentially useful in practising the methods of the invention.

According to another embodiment of the invention polyanhydrides may be used. These materials are knows for use as drug carrier matrices, and frequently have low glass transition temperatures (in some cases near normal body temperature) which makes them mechanically deformable with only a minimum of localized heating. Furthermore, polyanhydrides offer biodegradation times spanning from several months to several years depending on the particular polymer selected.

Additionally, copolymerization may be used to alter the molding temperature of many families of polymers. For example, although poly(epsilon caprolactone) homopolymers exhibit a melting temperature of approximately 60 degrees C., poly(epsilon caprolactone-co-lactic acid) copolymers containing approximately 20% lactic acid exhibit a reduced melting temperature of approximately 45–50 degrees C.

In one embodiment of the invention, the polymeric material is a polycaprolactone polymer having an indocyanine green or copper phthalocyanine dye compounded therein. Such dyes readily absorb light in the 780–800 nm wavelength range, a range that is available from semiconductor diode lasers. Furthermore, wavelengths in this range are not readily absorbed by body tissues or fluids, thus the possibility of physiologically intolerable levels of heating by absorption of the light energy by such tissues and fluids is minimized.

It is advantageous in some cases to deliver a drug or other therapeutic agent from the thermoformed polymeric structure. Such delivery has advantages that are well-known to those skilled in the art of drug delivery, including the ability to deliver the therapeutic agent to a specific location in the body and to achieve concentrations of the agent that are locally higher than could be attained practically and safely when the agent is delivered systemically. Intended therapeutic agents include, but are not limited to, growth factors and growth factor antagonists, mitotic and antimitotic agents, antibiotics, antimycotics, antioxidants, anti-inflammatory agents, and substrate analogs for enzymes or receptors.

In addition, the polymeric paving and sealing material may incorporate therapeutic agents such as drugs, drug producing cells, cell regeneration factors or even progenitor cells of the same type as the involved organ or histologically different to accelerate healing processes Such materials with incorporated therapeutic agents may be effectively used to coat or plug surgically or traumatically formed lumens in normally solid organs as well as the native or disease generated lumens of hollow or tubular organs.

The polymeric material used in PEPS can be combined with a variety of therapeutic agents for on-site delivery. Examples for use in coronary artery applications are antithrombotic agents, e.g., prostacyclin and salicylates, thrombolytic agents e.g. streptokinase, urokinase, tissue plasminogen activator (TPA) and anisoylated plasminogen-streptokinase activator complex (APSAC), vasodilating agents i.e. nitrates, calcium channel blocking drugs, antiproliferative agents i.e. colchicine and alkylating agents, intercalating agents, growth modulating factors such as interleukins, transformation growth factor 8 and congeners of platelet derived growth factor, monoclonal antibodies directed against-growth factors, anti-flammatory agents, both steroidal and non-steroidal, and other agents which may modulate vessel tone, function, arteriosclerosis, and the healing response to vessel or organ injury post intervention. In applications where multiple polymer layers are used different pharmacological agents could be used in different polymer layers. Moreover, PEPS may be used to effect pharmaceutical delivery focally within the vessel wall, i.e. media.

The polymeric material in accordance with the invention may also have incorporated in it living cells to serve any of several purposes. For example, the cells may be selected, or indeed designed using principles of recombinant DNA technology, to produce specific agents such as growth factors. In such a way, a continuously regenerating supply of a therapeutic agent may be provided without concerns for stability, initial overdosing and the like.

Cells incorporated in the polymeric material may also be progenitor cells corresponding to the type of tissue in the lumen treated or other cells providing therapeutic advantage. For example, liver cells might be implanted in the polymeric material within a lumen created in the liver of a patient to facilitate regeneration and closure of that lumen. This might be an appropriate therapy in the case where scar tissue or other diseased, e.g., cirrhosis, fibrosis, cystic disease or malignancy, or non-functional tissue segment has formed in the liver or other organ and must be removed. The process of carrying out such treatment involves first inserting a catheter into a lumen within a diseased organ segment. The lumen can be a native vessel, or it can be a man-made lumen, for example a cavity produced by a laser. The catheter is used to introduce a polymeric plug into the lumen. The catheter is then removed, leaving the plug in place to act as a focus for new growth stemming from cells implanted along with the polymeric plug. If the desire is for a more tubular structure, the plug can be appropriately reconfigured.

The polymeric material can incorporate biologically active molecules to impart additional properties to the polymer, such as resistance to bacterial growth or decrease in inflammatory response, as well as to encapsulate tissues. A wide variety of biologically active material can be encapsulated or incorporated, including proteins, peptides, polysaccharides, organic or inorganic drugs, nucleic acids, sugars, cells, and tissues.

Examples of cells which can be encapsulated include primary cultures as well as established cell lines, including transformed cells. These include but are not limited to pancreatic islet cells, human foreskin fibroblasts, Chinese hamster ovary cells, beta cell insulomas, lymphoblastic leukemia cells, mouse 3T3 fibroblasts, dopamine secreting ventral mesencephalon cells, neuroblastoid cells, adrenal medulla cells, and T-cells. As can be seen from this partial list, cells of all types, including dermal, neural, blood, organ, muscle, glandular, reproductive, and immune system cells, as well as species of origin, can be encapsulated successfully by this method. Examples of proteins which can be encapsulated include hemoglobin, enzymes such as adenosine deaminase, enzyme systems, blood clotting factors, inhibitors or clot dissolving agents such as streptokinase and tissue plasminogen activator, antigens for immunization, and hormones, polysaccharides such as heparin, oligonucleotides such as antisense, bacteria and other microbial organisms, including viruses, vitamins, cofactors, and retroviruses For gene therapy can be encapsulated by these techniques.

The biological material can be first enclosed in a structure such as a polysaccharide gel. (Lim, U.S. Pat. No. 4,352,883; Lim, U.S. Pat. No. 4,391,909; Lim, U.S. Pat. No. 4,409,331; Tsang, et al., U.S. Pat. No. 4,663,286; Goosen et al., U.S. Pat. No. 4,673,556; Goosen et al., U.S. Pat. No. 4,689,293; Goosen et al., U.S. Pat. No. 4,806,355; Rha et al., U.S. Pat. No. 4,744,933; Rha et al., U.S. Pat. No. 4,749,620, incorporated herein by reference.) Such gels can provide additional structural protection to the material, as well as a secondary level of perm-selectivity.

A second preferred application concerns a method of locally applying a biologically active substance to tissue surfaces of a patient. The biologically active substance can be any of a variety of materials, including proteins, carbohydrates, nucleic acids, and inorganic and organic biologically active molecules. Specific examples include enzymes, antibiotics, antineoplastic agents, local anesthetics, hormones, antiangiogenic agents, antibodies, neurotransmitters, psychoactive drugs, drugs affecting reproductive organs, and oligonucleotides such as antisense oligonucleotides.

In one embodiment, the polymeric material may comprise a stent that is applied to the interior of a blood vessel following treatment of a stenosis by angioplasty. In that embodiment, the material is provided in the form of a hollow sleeve having a diameter that allows it to be guided through a blood vessel using percutaneous transluminal techniques. Upon positioning the sleeve at the treatment site, the sleeve is heated to its molding temperature and radially expanded into contact with the wall of the vessel. Once expanded, the device is allowed to cool and become non-fluent, or harden, thereby providing a vessel lining that offers structural support to maintain the vessel open and facilitate blood flow. As such, the device prevents abrupt post-surgical closure of the vessel. Alternatively, the material may be expanded prior to heating and molding, this alternative being described in greater detail hereinafter.

In its numerous applications, the applied lining, such as a vascular lining may incorporate various therapeutic and pharmaceutical agents to provide a means for local delivery of such agents at the treatment site. For that example, in the case of blood vessels, such agents may be employed to further reduce the likelihood of restenosis or other unwanted conditions at the site. These may be incorporated in the device, or coated onto or absorbed into it. The device may have multiple layers to control migration of the therapeutic agent.

If the device does not include the perforations discussed previously, the lining may also serve to isolate the vessel wall from physiological fluids, and in so doing, may avoid one mechanism for restenosis. Although the mechanisms for restenosis remain unclear, there is some evidence to suggest that angioplasty damages portions of the blood vessel, and these damaged portions become sites for cell growth via interaction with certain components in the bloodstream. If the damaged vessel portion is isolated from the bloodstream, the possibility exists that initiation of restenosis may be avoided. Linings of this sort may be thinner, or less strong, than layers intended for use as structural supports.

In the embodiments described in detail below, including the preferred embodiment, the device and methods are used in intravascular therapy in situations where a guidewire is present, such as would be the case after a balloon angioplasty procedure. It is noted, however, that other cardiovascular treatments may not require certain elements shown in the figures. For example, if a catheter such as a guiding or sheath catheter remains in position from an earlier procedure, the guidewire (and thus the guidewire lumen) may not be necessary. Likewise, a central lumen may not be required if photothermoforming processes and materials are used in other organ systems, such as the intestines. Additionally, the devices depicted in the figures may include other features such as sensor or detector systems, or bypass lumens.

In one embodiment, the polymeric material may be delivered to the target site via a laser balloon catheter as shown in FIG. 1. The device 10 comprises an elongated flexible tube 11 (i.e., a catheter) having an article shaping element which comprises, for example, a radially expandable, inflatable balloon 12 positioned at its distal end. The tube 11 includes an inflation lumen 13 through which the balloon 12 may be inflated, The tube 11 also includes a central lumen 14 adapted to engage a guide wire. The central lumen 14 also allows passage by an optical tip assembly 15 which comprises a radial light diffuser 16 connected to a light source/controller 17 via an optical fiber 18.

The radial light diffuser 16 may comprise a flexible, translucent tube containing a light-scattering filler such as those described below with respect to FIGS. 2a and 2b. In one embodiment, the diffuser 16 contains a transparent or translucent adhesive containing light-scattering $TiO_2$ particles. The optical fiber 18 is connected between the high source/controller 17 and the radial diffuser 16 and serves to transmit light between the source and the diffuser. When activated, the source produces light which travels through the optical fiber 18 and into the diffuser 16 causing the light to be scattered in a generally uniform, radial manner. As an alternative, portions of the diffuser may be masked or otherwise rendered non-translucent to produce radial or axial non-uniformities in the scattered light. Both the balloon 12 and the portion of the tube 11 in the region of the balloon should be substantially transparent to the light emitted from the diffuser.

The use of device 10 and other devices of the invention is described hereinafter. It should be understood that aspects of the invention described in greater detail below with respect to FIGS. 2–7 are applicable to the embodiment illustrated in FIG. 1.

Figure 2A:
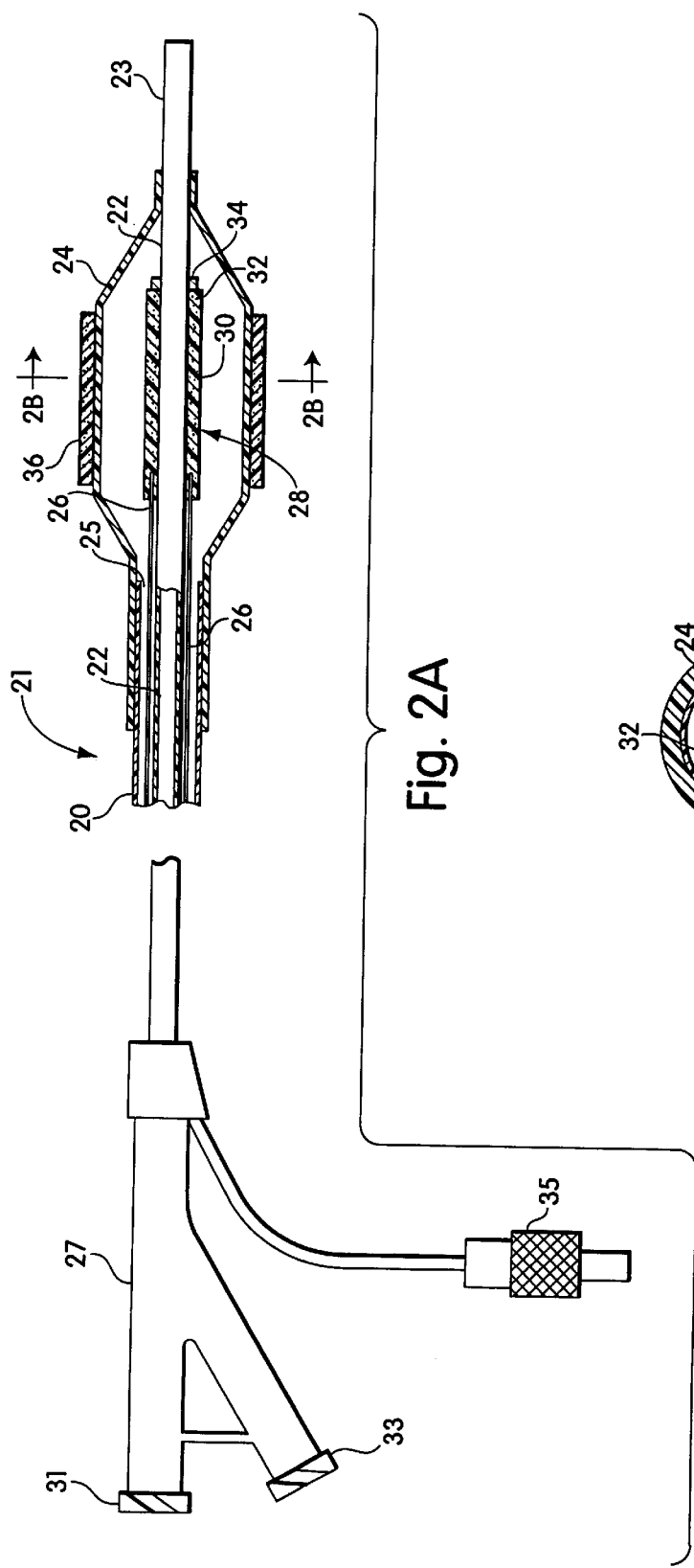
FIGS. 2a and 2b illustrate one embodiment of a laser balloon catheter suitable for delivery of a to polymeric material.
Figure 2B:
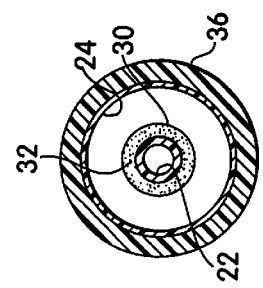

Another embodiment is illustrated in FIGS. 2a and 2b. The device 21 comprises an outer elongated flexible tube 20 (i.e., a catheter) and an inner elongated flexible tube 22 positioned within the lumen of the outer tube 20. The inner tube 22 is longer than the outer tube 20 so as to cause its distal end 23 to extend distally beyond the distal end of the outer tube 20. An article shaping element, for example a radially expandable, inflatable balloon 24 is mounted on the distal end of the device such that the proximal end of the balloon 24 is secured near the distal end of the outer tube, and the distal end of the balloon is secured near the distal end of the inner tube. As will be described in detail below, a moldable polymeric article 19 is positioned on the balloon prior to its implantation at a desired treatment location.

The annular space formed between the inner wall of the outer tube and the outer wall of the inner tube forms an inflation lumen 25 through which the balloon may be inflated and expanded, Positioned within the annular space is at least one, and preferably a plurality of optical fibers 26 which extend from the proximal end of the device and have distal ends which communicate with an optical emitter assembly 28. The optical emitter 28 is positioned within the interior of the balloon and preferably comprises an integral part of the inner tube 22 in the region in which the inner tube passes through the balloon. The article shaping element is not intended to be limited solely to a radially expandable balloon. Numerous other shaping elements, including but not limited to malecots and the like are contemplated as well.

In one embodiment, the optical emitter 28 delivers diffuse light within the shaping element and comprises a flexible, translucent tube 30 containing a light-scattering filler 32. The filler can comprise a translucent matrix containing light-scattering media such as titanium dioxide ($TiO_2$) particles. Other light scattering media include $Zr_2O_3$, $Ba_2SO_4$, diamond dust, glass beads, and combinations thereof, with or without $TiO_2$. The translucent matrix can comprise, for example, an epoxy or other polymeric material which fills the annular gap between the translucent tube 30 and the inner tube 22, thereby forming the emitter as an integral element of the inner tube.

The proximal end of the device includes a hub assembly 27 having a port 31 to access the lumen through inner tube 22, a balloon inflation port 33 communicating with inflation lumen 25, and an optical fiber connector 35 which is attachable to a light source (not shown) to provide light through the optical fibers 26 to the optical emitter 28.

Figure 3:
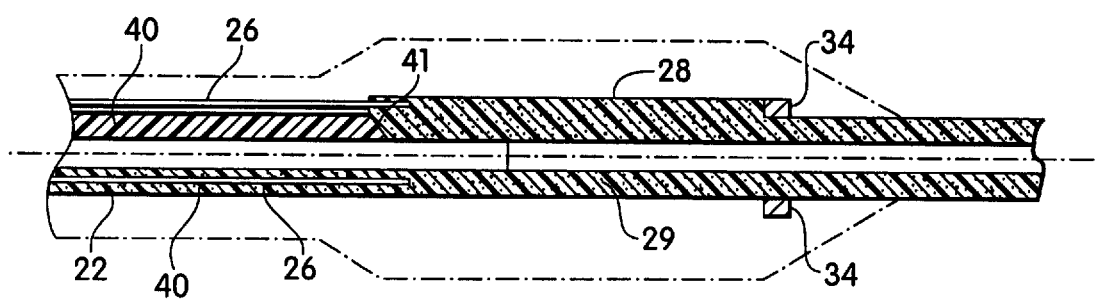
FIG. 3 is an illustration of a laser balloon catheter showing two embodiments of an optical emitter.

Two alternate embodiments for the emitter are shown in FIG. 3. In each of those alternate embodiments, the emitter may comprise the distal end of the inner tube, in the portion extending through the balloon and beyond its distal end. In the first alternate embodiment, shown in the upper portion or FIG. 3, the emitter 28 is affixed to the distal end of a catheter tube 40 using a taper joint 41, a lap joint, or other known joint structures to form a tubular assembly having a light diffusing distal end. The emitter preferably comprises a translucent polymer having an inherent light-scattering characteristic or a light-scattering medium compounded therein. Optical fibers 26 communicating with the emitter are provided within the annular space between the outer and inner tubes or within lumens provided in the inner tube. In the second alternate embodiment, shown in the lower portion of FIG. 3, rather than comprising a two-piece construction as shown in the upper portion of FIG. 3, the catheter tube 40 may be translucent with light-scattering characteristics along all or part of its length. In that case the emitter is defined as that portion 29 of the tube 40 located distally to the distal ends of the optical fibers. It should be understood that FIG. 3 is a composite of two alternate embodiments of the device, and that in the actual device both the upper and lower portions would be the same.

The distal ends of the optical fibers 26 terminate within the light-scattering filler to allow light exiting from the fibers to be scattered in a substantially uniform radial manner. A light source/controller (not shown) is connected to the proximal ends of the fibers and serves to transmit light through the fibers into the emitter. By varying the concentration and composition of the scattering particles, and the number, position, and shape of the distal ends of the optical fibers, the intensity of the light field in the axial and circumferential directions can be controlled. Methods for achieving desired distributions of light intensity are known in the art and include simply arrays of scattering particles embedded in plastic as exemplified in U.S. Pat. No. 5,169,395 to Narciso, Jr.; and gradients of scattering particles as exemplified in U.S. Pat. No. 5,196,005 to Doiron et al.

It is noted that the emitter need not comprise a tube filled with a scattering material. Rather, a solid tube or annular sleeve of a material having inherent scattering properties such as polyethylene or PTFE may be substituted.

Returning to FIGS. 2a and 2b, the flexible, translucent tube 30 of the emitter comprises a flexible material which minimizes absorption of light in the wavelength spectrum provided by the light source/controller. Numerous translucent polymeric materials can be used, including polyethylenes (PE), polyethylene terephthalates (PET), and polyfluoroalkylenes such as PTFE. Polyethylene is preferred. The light scattering filler 32 preferably comprises a transparent or translucent matrix, for example an epoxy adhesive, containing the light-scattering particles. The filler 32 is contained in the annular space created between the interior of the emitter tube 30 and the exterior of the inner tube 22. Like the emitter tube 30, the matrix containing the light-scattering particles must be substantially transparent to the wavelength spectrum of light produced by the light source/controller. Similarly, the balloon itself and its inflation medium must be transparent to the light in order to allow the light to pass through the balloon and heat the polymeric particle positioned on the balloon. A preferred inflation medium comprises a mixture of equal parts of saline and an iodinated contrast agent. Such a mixture is sufficiently transparent to light from the emitter and also radiopaque to aid fluoroscopic visualization.

As an alternative, the emitter may be formed integrally with the distal end of the optical fibers themselves. For example, the distal end of the fibers may be chemically or mechanically modified in a manner which causes the fibers to radiate laterally in the region of the modification. Thus, in one embodiment, the distal end of the fibers may be ground or chemically modified to "frost" the fiber, thereby to provide light scattering sites directly on the fiber surface. Optical fibers modified in this manner simplify manufacture of the devices in that the need to assemble a separate optical emitter for use with the device is eliminated.

In one embodiment, the inner tube 22, at least in the region of the optical emitter 28, is transparent to light in the wavelength spectrum being used to prevent "shadowing" of the light. As an alternative, a reflective coating may be armed about the inner tube 22 in the region of the optical emitter to reflect back any light scattered toward the inner cube 22 by the light scattering medium. If the inner tube 22 is translucent, the reflective coating can be provided on the inner surface of the tube. For light in the visible spectrum, the reflective coating preferably comprises a thin coating of silver, and for light in the infrared spectrum, the reflective coating preferably comprises a thin coating of gold. Such coatings can be deposited using any of a variety of known methods for depositing metal on polymeric surfaces, including but not limited to sputtering, ion bombardment, and ion-assisted vapor deposition. It is noted that these modifications are not mandatory, however, as satisfactory results can still be achieved even if the inner tube 22 in the region of the optical emitter 28 is not reflective of or translucent to the light. If the inner tube absorbs light in the wavelength spectrum provided to the polymeric article 36, the tube must be fabricated of a material that has a melting or glass transition temperature sufficiently high to avoid deformation of the tube during the heating and forming process.

A radiopaque marker 34 such as a band or ring or tantalum, gold, tungsten or silver, may be positioned on the device in order to aid the physician in determining the location of the distal end of the device during an implantation procedure. As shown in FIG. 2a, the radiopaque marker may be positioned within the interior of the balloon, however, other positions may be used as well. Furthermore, the device is not limited to the use of a single marker, but rather may make use of a number of such markers positioned at various places on the device.

The first and second elongated tubes can be formed of polymeric materials comprising, for example, polyethylenes, nylons, polyvinyl chlorides, polyether block amides, polyurethane, and combinations and copolymers thereof. The balloon preferably comprises a polymeric material such as polyethylene terephthalate, crosslinked polyethylene or composites thereof.

In order to ensure that the polymeric article does not stick to the balloon during the implantation procedure, the balloon may have a coating formed of a low surface energy material on its outer surface. Examples of such coatings include surfactants, hydrogels, fluoropolymers or silicone-based coatings. In the alternative, the surface of the balloon may be modified to a low energy surface using a plasma treatment, or the balloon itself may be made of a material with low surface energy (i.e., crosslinked polyethylene). Likewise a low surface energy properties can be provided on the polymeric article on surfaces which contact the balloon.

In an alternate embodiment, depicted in FIGS. 4a and 4b, the implantation device 50 can comprise an elongated tubular body 52 having at least two lumens extending from its proximal end. A central lumen 54 extends through the entire length of the tube, thereby allowing fluids and devices, such as guidewires, to pass entirely through the tube. At least one balloon inflation lumen 56 provides communication between the proximal end of the tube 52 and the interior of a radially expandable balloon 58 mounted near the distal end of the device. An optical emitter 60 is positioned within the balloon and serves to scatter light provided by at least one, and preferably a plurality of optical fibers 62 in a substantially uniform manner. The optical fibers can communicate with the emitter 60 either through the balloon inflation lumen 56, or, in the alternative, through a separate optical fiber lumen provided in the tubular body 52. A moldable polymeric article 36 is positioned on the balloon 58 prior to its implantation at a desired treatment location.

As in the embodiment described in connection with FIGS. 2a and 2b, the optical emitter 60 may surround a portion of the tube 52 passing through the balloon, or, in the alternative, it can comprise the distal portion of the tube. Thus, the emitter can be of similar constructions as those described in connection with the earlier embodiments and as depicted in FIGS. 2a and 2b or FIG. 3. Also as in the earlier embodiment, one or more radiopaque markers 66, such as tantalum bands, may be positioned on the device to aid the physician in determining the location of the distal end of the device during an implantation procedure. Additionally, the proximal end of the device includes a hub assembly 27 having a lumen access port 31 to access the central lumen 54, a balloon inflation port 33 communicating with one or more balloon inflation lumens 56, and an optical fiber connector 35 in communication with the optical fibers 26.

When more than one balloon inflation lumen is provided, the ability to flow chilled fluid through the balloon is realized. For example, chilled fluid such as saline may be introduced into a first balloon lumen, allowed to flow through the balloon, and to exit the balloon through a second lumen. In this way, the polymeric article may be cooled, hastening its return to a non-fluent state and potentially preventing or minimizing thermal damage to tissue.

In each embodiment described herein, the device need not be limited solely to catheters having a central lumen passing entirely though the catheter shaft. Rather, the catheters can include a separate, shorter lumen having one end which exits the catheter at or near the distal end of the catheter shaft and a second opening somewhat proximal to the distal end of the shaft. Such so-called "rapid exchange" or "monorail" catheters are designed to facilitate catheter exchanges while maintaining positioning of a guidewire. Monorail catheters are known in the art, being described, for example, in U.S. Pat. No. 4,762,129 to Bonzel.

In each embodiment, portions of the emitter or the shaping element optionally can be masked or otherwise rendered nor-translucent to produce radial or axial non-uniformities in the scattered light if non-uniform heating of the polymeric article 36 is desired.

In each embodiment, the device can be used as follows. The balloon is deflated and a polymeric article is positioned about its exterior. The balloon carrying the polymeric article is then advanced through a body lumen to position the polymeric article at a desired treatment location. Once positioned, light energy is supplied from the source through the optical fibers to the optical emitter or optical tip assembly. The light diffuses outwardly from the emitter and through the balloon (and through a tube according to the embodiment illustrated in FIG. 1). Upon transmission through the balloon, the light energy is absorbed by the polymeric material or by chromophores contained in the material. The energy absorption heats the polymeric material to at least its molding temperature. Once the molding temperature has been achieved, the balloon is inflated fully, thereby molding the material into conforming contact with the adjacent tissue surface. By providing an article that absorbs light in the wavelength spectrum supplied by the source, the article may be rapidly bulk heated with only minor conductive loss of heat to the surrounding tissue.

It should be understood that the sequence of heating and molding steps is not intended to be the sole method for implanting the polymeric article. For example, in an alternative embodiment, the balloon may be pressurized prior to heating of the polymeric article. In that embodiment, the pressurized balloon presses against the interior surface of the polymeric article which yields upon subsequent heating to its melting or glass transition temperature, thereby allowing the balloon to mold the material into conforming contact with the adjacent tissue surface. In still another embodiment, if the polymeric article is of a shape that can be expanded prior to becoming moldable, the article can be guided to a desired treatment location and then expanded by a partial inflation of the balloon. Upon heating the article to its molding temperature, the balloon can then be fully inflated, hereby molding the previously expanded article into conforming contact with an adjacent tissue surface.

Once the article has been molded, the light energy is discontinued, thereby allowing the material to cool and become non-fluent. Either during or after the cooling process, the balloon is deflated and the catheter withdrawn, thereby leaving an expanded polymeric material lining positioned at the treatment site. In one embodiment, the polymeric article may comprise a relatively thin sheet of material that is positioned upon a tissue surface during a surgical procedure. Upon heating to a temperature above its molding temperature, the sheet may be pressed against the tissue surface, thereby causing it to conform to the surface shape. Alternatively, the sheet may be rolled about the balloon portion of the previously described balloon catheter. Upon heating to its molding temperature and expansion of the balloon, the sheet is caused to unroll and to be pressed into conforming contact with the interior of a body lumen. The ends of the sheet may be sealed to form a tubular structure. In another embodiment, the article may comprise a pleated, accordion-like shape which upon heating may be expanded to cover a surface.

According to still another embodiment, the sheet or pleated article may be first expanded, and then heated and molded in the manner described above.

Figure 5A:
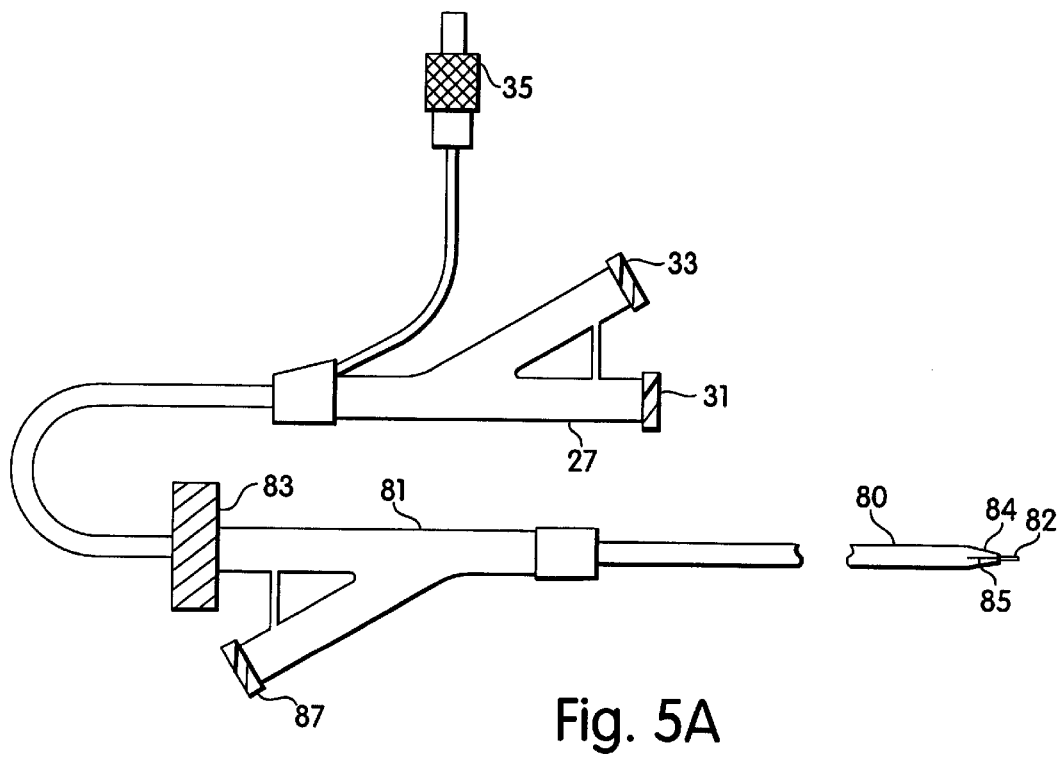
FIGS. 5a and 5b illustrate a retractable sheath suitable for use with the laser balloon catheters of FIGS. 1, 2 and 4.

In each of the embodiments described above, the device may include an elongated retractable sheath as an aid to maintaining the polymeric article on the balloon during the period at which the device is guided to the treatment location. As shown in FIG. 5a, the sheath 80 comprises a retractable elongated tube which is operatively coupled to or extends from the proximal end of the implantation device to a point distally beyond the shaping element. The distal end 82 of the implantation device may extend a short distance beyond the end of the sheath.

The sheath optionally can include a tapered distal tip 84 formed of a relatively soft, radially expandable material that may include at least one longitudinal slit 85 formed therein. The tip is affixed to the distal end of the sheath using, for example, a taper or lap joint. Alternatively, the tip 84 can be an integral part of the sheath 80. The use of a soft, pliable material and/or slits allows the tit to expand radially, thereby allowing the sheath to be withdrawn over the shaping element. The tapering of the tip provides a shaped surface which is adapted to minimize the possibility of damage as the distal end of the device is guided through a tissue lumen by providing a low profile leading edge.

The hub assembly 27 is as described above. However, an additional hub 81 is provided. Additional hub 81 is operatively connected to sheath 80 and serves as an actuator to retract the sheath and also as a hemostatic valve. A collar 83 positioned at the proximal end of hub 81 allows the practitioner to retract the sheath 80 and expose at least a portion of the implantable polymeric article 36. An optional port 87, in communication with the interior of the sheath, is provided. The port 87 allows fluid to be injected between the sheath and the portion of the device surrounded by the sheath if so desired.

Figure 5B:
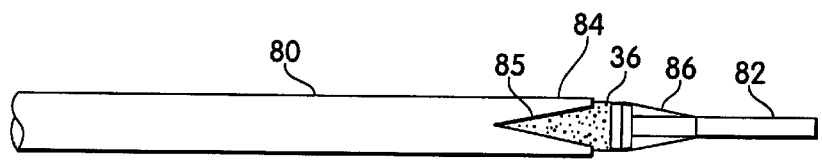

As shown in FIG. 5b, upon positioning the polymeric article 36 at the desired location, the sheath is retracted to expose at least the article 36 and the underlying balloon 86. The tip is radially expandable with a minimum of force to allow the sheath to be retracted, thereby pulling the tip over the polymeric article, without dislodging the article from the balloon. The sheath is preferably formed of a polymeric material selected from the group consisting of fluoropolymers, high density polyethylenes, polyether block amides, polyurethanes, thermoplastic elastomers, and combinations and copolymers thereof. If used, the tapered distal tip preferably is formed of soft, flexible materials such as natural or synthetic rubbers, silicones, polyether block amides, polyurethanes, thermoplastic elastomers, and combinations and copolymers thereof.

The use of a retractable sheath is optional, as static friction between the article and the balloon may be such that the article will not become dislodged from the balloon as the device is guided to a treatment location. Alternatively, other mechanical means such as end caps, or other retainers known in the stent art may be used to retain the article on the balloon. In particular, retaining sleeves or grommets of silicone or other polymers, positioned proximally and, optionally, distally of an article positioned on a balloon, can be used to retain articles in position on the balloon during passage through the body to a delivery site, or upon withdrawal of the retractable sheath.

Figure 6A:
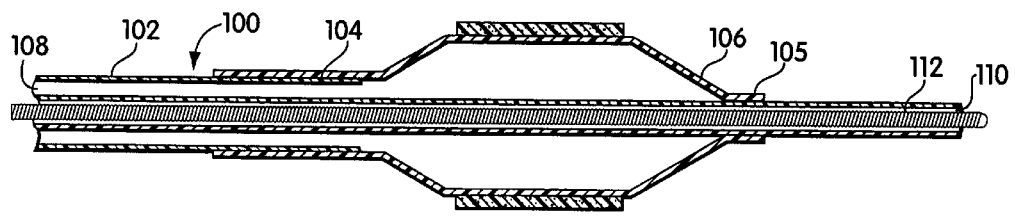
FIGS. 6a and 6b are schematic illustrations of another embodiment of a device for providing a thick polymeric film on a luminal wall.
Figure 6B:
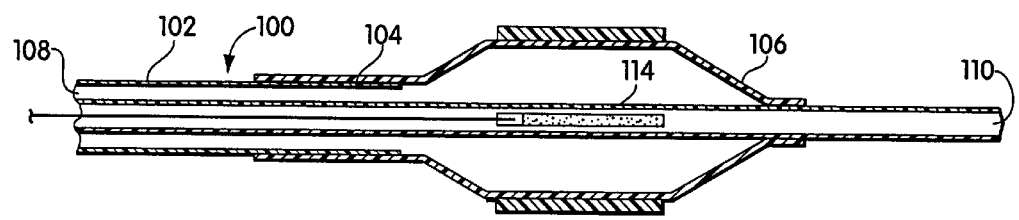

Still another embodiment of the device is depicted schematically in FIGS. 6a and 6b. In that embodiment, the optical emitter is not included as part of the balloon catheter assembly, but rather, comprises a separate element that is inserted through the central lumen of the balloon catheter during the treatment procedure. More particularly, such a device 100 comprises a balloon catheter 102. The balloon catheter 102 comprises an outer elongated tubular shaft 104 and an inner elongated tubular shaft 105 having a shaping element 106 such as an inflatable balloon affixed near the distal ends of the shafts 104 and 105. One or more radiopaque markers may be positioned on the shafts 104 and 105. A central lumen 110 extending through the inner catheter shaft 105 is used to accommodate a guidewire 112, as well as an optical emitter as described below. If the shaping element 106 comprises an inflatable balloon, the balloon is inflated and deflated using a molding lumen 108. At least the portion of the inner shaft 105 in the area of the shaping element 106, and the shaping element itself, must be sufficiently transparent to allow light provided by an emitter positioned in the central lumen to pass through the shaft and the shaping element to an extent sufficient to allow heating of a polymeric article mounted on the shaping element.

As shown in FIG. 6b, the device 100 further includes a separate optical emitter 114 that may be inserted through the central lumen 110 once the guidewire 112 is removed. The emitter may be of the type shown in FIGS. 7a or 7b. In the embodiment depicted in FIG. 7a, the optical emitter 114 has, at its distal end, a flexible, translucent emitter tube 116 containing a light scattering filler 118, such as that described previously. At least one optical fiber 122 has its distal end terminating within the light scattering filler 118. The proximal end of the optical fiber 122 terminates in an optical fiber connection 35 which is used to connect the optical fiber to the light source/controller (not shown). The emitter tube 116 is formed of a material that is substantially translucent or transparent to the light delivered through the optical fiber. Numerous translucent polymeric materials can be used, however, polyethylene is preferred.

Figure 7A:
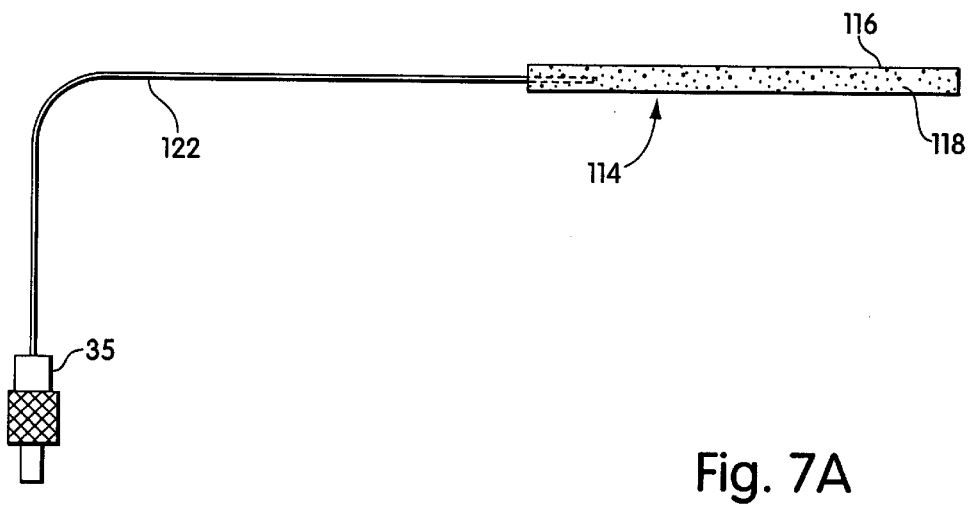
FIGS. 7a and 7b are schematic representations of an optical emitter catheter for use with the device of FIG. 6b.
Figure 7B:
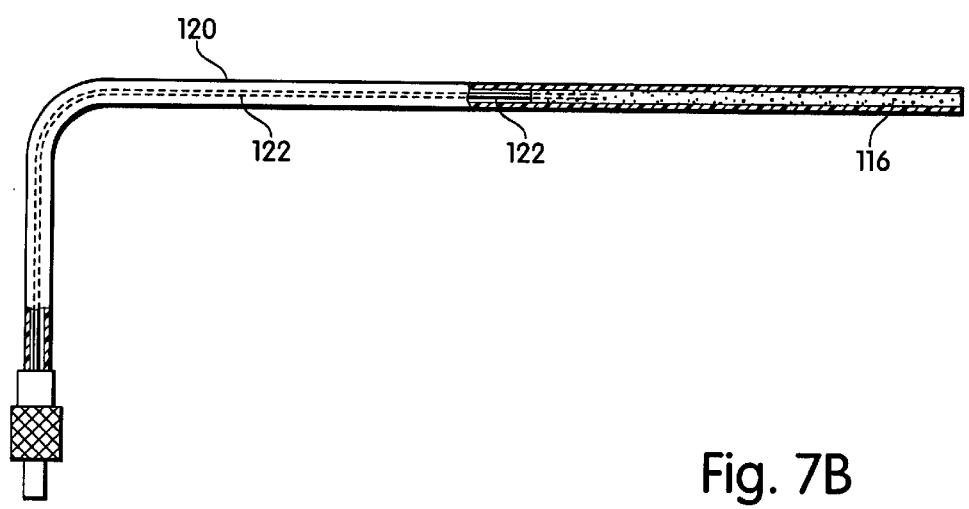

As an alternative, shown in FIG. 7b, rather than mounting the emitter tube 116 on the distal end of the optical fiber 122, an emitter 130 comprising an emitter tube 116 and an emitter shaft 120 may be used. The emitter tube 116 may comprise a single integral shaft formed of a translucent or transparent material and loaded with the light scattering filler. The emitter tube 116 may be a separate element joined to the distal end of the emitter shaft 120, or it may be an integral element of that shaft. In the latter case, the emitter shaft can have light scattering properties along its entire length, or it may be a clear or translucent tube having scattering properties only at its distal end.

As still another alternative embodiment, at least one optical fiber having its distal end modified, for example by chemical or physical processes, so as to radiate light laterally can be substituted for the emitters described above. For example, disruption of the cladding of the optical fiber, such as by abrasion, allows control of the lateral emission profile.

In use, the device illustrated in FIGS. 7a and 7b is positioned at a treatment site, typically post-angioplasty, using percutaneous transluminal catheterization procedures. Prior to insertion into a human or animal patient, the molding balloon is deflated and a polymeric article to be implanted is mounted on the balloon. If the procedure is to be carried out post-angioplasty, the angioplasty guidewire is left in place. However, if the procedure is to be carried out at some other time, a guidewire is first introduced into a patient and navigated until its distal end crosses the treatment location. The device is passed over the guidewire until the molding balloon and polymeric article is positioned at the treatment location. The guidewire is then withdrawn.

Once the guidewire has been withdrawn, the optical emitter 114 or 130 is inserted through the central lumen of the balloon catheter shaft 104 and advanced to position the emitter tube 116 in the portion of the shaft surrounded by the molding balloon 104. Light is then directed to the emitter to render the polymeric article positioned about the molding balloon moldable. As before, the molding balloon can be inflated either before, during, or after providing light to the emitter, Once the polymeric article has absorbed enough light to be heated to a point at which it becomes moldable, it is expanded, by the molding member, into contact with the adjacent lumen walls. Once the article has been expanded, the light supply to the emitter is terminated, the molding balloon is deflated, and the device is withdrawn, leaving the polymeric article in position at the treatment site.

Rapid solidification of the polymeric article after cessation of irradiation is desirable in many contemplated applications. Addition of nucleation centers into the polymeric material can accelerate the increase of strength of the material during cooling by increasing the crystallization temperature and rate of the material. The use of nucleating agents is described in U.S. Pat. No. 4,444,927 to Borysko, and in an article entitled, "A Nucleating Agent for Crystalline Olefinic Polymers", by Carroll, Modern Plastics, 108 (September 1984), the entire contents of both of which are incorporated herein by reference for all purposes. For example, sucrose, lactose, dibenzylidene sorbitol, or a combination of these may be included in the polymeric material of the invention at a concentration of up to about 2 percent by weight, preferably about 0.5 percent by weight.

The polymeric article and the balloon material must be selected such that the article does not stick to the balloon surface regardless of whether the article is above or below its molding temperature. If necessary, a non-stick coating may be applied to the exterior of the balloon or to the interior of the article to allow the article to be released from the balloon following molding. When a non-stick coating is applied, it may be particularly advantageous to employ the above-described sheath or mechanical means such as end caps or other retainers to retain the article.

The method of the present invention is not intended to relate solely to systems in which the polymeric material cools and hardens by dissipating heat into physiological tissues and fluids in its immediate area. Rather, accelerated cooling may be achieved by contacting the heated material with a cooling fluid such as chilled saline, as discussed above.

In one embodiment of the invention, a means is provided for determining that the polymeric material has achieved its molding temperature in order to allow the physician to begin the thermoforming procedure. In that embodiment, the means used to reshape the material can also be used to indicate that the molding temperature has been achieved. For example, if the material is to be molded using a dilatation balloon surrounded by the material in its initial, predeployment configuration, the balloon may be pressurized continuously during the heating process. Once the material becomes moldable, it will yield, allowing the balloon to expand. Such an expansion can be detected directly by the physician, or by a pressure or mass flow transducer in communication with the balloon inflation lumen. Other sensor systems may be used, including optical reading of temperature via a thermochromic dye, or direct temperature measurement by a probe. If a detector is used, it may also be used to shut off the light source used to heat the material once expansion occurs.

The use of thermochromic dyes, as discussed above, may facilitate accurate temperature measurement of the polymeric material. For example, in the case of polycaprolactone compounded with indocyanine, it has been observed that the material transforms from its characteristic green color to a translucent, clear appearance upon reaching its molding temperature. Subsequently, upon cooling and solidifying, the material returns to its previous green color. These colorations may be detected using remote reflectant photodetectors and optical fibers as are disclosed in U.S. Pat. No. 5,009,655 to Daignault, Jr. et al.

As described previously, the polymeric article may contain apertures or other discontinuities which remain once the article has been molded. Likewise, the article may be any of a broad range of shapes suitable for molding in vivo. For example, the polymer may be in the form of a perforated tubular sleeve, a helical sleeve, a braided sleeve, or a plurality of discontinuous members of various shapes.

The polymeric materials of the present invention may be combined with a variety of therapeutic agents or living cells. The incorporation of therapeutic agents and/or cells is described in detail in the previously mentioned International Publication of Slepian et al.

In addition to blood vessels, the method of the present invention may be used for providing polymeric linings and coatings to other body organs including but not limited to ureters, urethrae, bronchi, biliary and pancreatic duct systems, the trachea, the gut, the eye and the spermatic and fallopian tubes, The method can also be used in other direct clinical applications including, but not limited to, treatment of a blood vessel closure following coronary angioplasty, repair of vessel dissections, sealing of vessel wall flaps occurring either spontaneously or secondary to injury, sealing of aneurysms, and the like. In addition, the method provides a means for intra-operative sealing of vessel anastomoses during coronary bypass grafting, as well as a method for providing a "bandaged" smooth polymer surface following endarterectomy procedures.

As noted earlier, the method provides for "customizable" deployment geometry capabilities to accommodate numerous complex organ or vessel surfaces. The customized geometry can be provided using structurally stable polymers that may be tailored to correspond to the surface of a body tissue. By applying the polymeric material in moldable form, the material can be caused to coat uneven surface interstices. The resulting polymeric structure will facilitate improved structural support for numerous applications including eccentric coronary lesions which, by virtue of their geometry, are not well bridged using conventional stents.

The initial predeployment design and size of the polymeric structure will be dictated to some extent by the specific application and by the final deployed physical, physiological, and pharmacological properties desired. In the case of coronary artery applications, predeployment sleeves having a length of approximately 10–20 mm and a diameter of approximately 0.5–2 mm are preferred. The wall thickness of the resulting in vivo polymeric layer will vary depending on the nature of the particular application. In general, procedures adapted to provide a thin polymeric layer to a tissue surface will use polymer layers having a thickness of approximately 0.005–0.2 mm, while layers which are designed to provide structural support to a vessel may vary in thickness from approximately 0.05–0.5 mm. The ultimate dimensions of the polymeric layer will depend upon the tissue to be treated. For example, within a cone lumen, a coating thickness of up to 5 mm may be beneficial. Thus, the suggested thickness are not intended as limitations.

A predeployment polymer tube for application in tissue lumens may be single or multi-layered and may be processed prior to insertion using laser or chemical etching, pitting, slitting or perforation depending upon the application. Additionally, the shape of any perforation may be further geometrically modified to provide various surface areas on the inner and outer surfaces of the polymeric article.

It is contemplated that the polymeric structures may be coated, either before or after placement, to obtain a surface suitable for the therapeutic surface. For example, the surfaces of a predeployed polymer may be further modified with bound, coated, or otherwise applied agents such as cyanoacrylates or biological adhesives to assist in adhering the material to a tissue surface. In particular, the surface may be coated to achieve or maintain biocompatibility or bioinertness with respect to blood, tissue or other materials, especially with respect to blood. Any of the biocompatible coatings known in the art may be used, such as heparin, or coatings containing polyethers or polyalkyleneglycols.

For applications involving the coronary arteries, the predeployment polymer tubes may include perforations or pores to provide symmetrical or asymmetrical expansion of the polymeric material. By using a polymer tube having openings or perforations, significant mechanical stability is provided, while minimizing the amount of foreign material (i.e., polymer) placed into the blood vessel. Perforations may encourage more rapid and complete encapsulation of the polymeric stent, which may be desired to prevent distal embolization.

The methods and materials have numerous other therapeutic applications. For example, the material may be used to provide a barrier layer on tissue surfaces to prevent the formation of connective tissue following trauma or surgical injury, or the material may be used to adhere tissue surfaces to other tissues or implants. In one embodiment, the adherent properties of the materials may be used to join severed nerve endings. These and other applications are described in detail in copending U.S. application Ser. Nos. 07/843,485 and 07/870,540 to Hubbell et al., incorporated herein by reference.

The ultimate in vivo deployed geometry of the polymer dictates the final function of the polymer coating. Thinner applications allow the polymer film to function as a coating, sealant, partitioning barrier, bandage, and/or drug depot. Complex internal applications of thicker layers of material, such as intra-vessel or intra-luminal applications, provide increased structural support to maintain vessel or organ patency while providing the above features.

Vessel walls and lesions which are comprised mostly of fibromuscular components have a high degree of viscoelastic recoil. Such lesions require the application of an intra-luminal coating of greater thickness so as to impart more structural stability and to resist radial compressive forces. The inventive process may be used to provide structural stability and is thus generally applicable for the maintenance of intra-luminal geometry of all tubular biological organs or structures. It may be used in this manner following therapeutic return of normal architecture associated with various procedures known in the art.

In its simplest form the polymeric structure may be composed of an homogenous single layer. However, optimal light absorption and heat transfer within the device may be achieved by using gradients of absorber within the structure, or multiple layers of polymer with different concentrations of absorber. This can alleviate the attenuation of light at the outer surface caused by absorption within the polymeric structure. Multiple layers may also be used to selectively deliver drug to the surrounding tissue, or to the lumen of the hollow organ or passage, by making one side of the structure less permeable to the drug.

Specific objects and features of the present process are best understood by way of illustration with reference to the following examples.

EXAMPLES

Example 1
Hydrophilic Dye in Poly(e-caprolactone)

A hydrophilic dye, indocyanine green (IG), was dispersed in poly(ε-caprolactone), (PCL), a hydrophobic polymer, by solvent blending. The IG was dissolved in a drop of dimethylsulfoxide and was added to a 20% w/w solution of PCL in acetone. The resulting uniform solution was then cast in the form of films 130 micron (micrometer) and 250 micron thick, using a casting knife. The films contained 1 mg of IG per gram of PCL and the 250 micron films had an absorbance of 0.5 A.U. at 780 nm.

A sheet of the dye-containing polymer having a thickness of 250 micron was illuminated with an incident spot size of 1 cm diameter and raised to a temperature above its melting point of 63 degrees C by the application of approximately 4 joules of 780 nm light. The energy was applied at the intensity of 0.5 watts applied onto the 1 cm diameter spot for eight seconds. By demonstrating that the material sample could be sufficiently melted in this short period of time, it was shown that a phase change could be achieved in the polymer while using energy levels and time periods that are satisfactory for use in vivo.

The example further illustrates how a hydrophilic dye can be dispersed into a hydrophobic polymer, and also that near infrared light, which is poorly absorbed by tissues, can be used to melt the polymer in a short period of time.

Example 2
Hydrophobic Dye in Poly(e-caprolactone)

A hydrophobic dye, ethyl eosin (EE), was dispersed in. PCL by solvent blending using acetone. The EE was dispersed in the PCL at a concentration of 1.5 mg per gram of PCL. A 200 micron thick film of polymer was solution cast. A sheet of polymer was illuminated with an argon-ion laser at an intensity of approximately 250 mW/cm$^2$ at all visible lines, including 514 nm. The melting took place within 5 seconds and could be detected by the change to a clear melt from the translucent semi-crystalline polymer film. The transmission of 514 nm light through this film was less than 5%. No photobleaching of the dye was evident over the period of the melting process.

This example illustrates how a hydrophobic dye can be dispersed into a hydrophobic polymer. It also illustrates that visible light, can be used to melt the polymer within a short period of time and that small amounts of light are transmitted through the polymer film. This would minimize any tissue heating and trauma that could possibly occur by irradiation from the visible light.

Example 3
Blood Compatible Coating for Intravascular Stenting

A polycaprolactone/ polyethylene oxide (PEG) block copolymer was synthesized by standard procedures. 37.5 g of PEG, molecular weight 8000, was heated in a 3-arm reaction flask at 90 degrees C overnight under vacuum, and then purged with nitrogen to complete drying. Caprolactone (12,5 g) was weighed into a sealed Erlenmeyer flask with a septum, and 29 microliters of a 10% w/v solution of stannous octanoate in chloroform was injected. The flask was shaken to dissolve the catalyst in the caprolactone. The caprolactone solution was adder in an anhydrous manner (direct transfer) to the molten PEG, and the mixture was heated with stirring to 180 degrees C for 3 hours and allowed to cool under nitrogen purging until room temperature was reached. The polymer was dried overnight under vacuum at 90 degrees C. Polymer was removed from the reaction flask while molten, in a nitrogen-filled glove bag, and kept anhydrous until use.

Example 4
Paving Devices for Prototype Clinical use in Animals

All steps below are at room temperature and in normal air unless otherwise stated. Indocyanine green (37.6 mg) was dissolved in 360 microliters of dimethylsulfoxide and diluted with 36 ml of chloroform. Polycaprolactone (3.65 g) of molecular weight about 80,000 was added to the dye mixture. The mixture was tumbled overnight in a capped tube to complete the dissolution. Thin films about 0.0015 inch (about 37.5 microns) thick were cast on glass plates, allowed to air dry, and then dried in a vacuum oven at 50 degrees C overnight.

The film was stripped and folded to be four layers thick, and then pressed at 80 degrees C in a Carver press at 5000 psi (about 350 bar) to a thickness of about 0.0045–0.0050 inch (113–125 microns). Apertures, about 1 mm in diameter, were made in the film using a template and sharpened hypodermic needle tubing. About 25% of the surface area was removed, in a square array. Radiopaque markers (platinum foil) were affixed beneath a single layer of the same film, and the assembly was bonded by passage through a laminating press set at 65 degrees C.

Some devices were coated at this stage with the polymer of example 3. They were affixed to a piece of filter paper, and sprayed for 5 to 10 seconds with a freshly-prepared solution containing 10% of the example 3 polymer in 75:25 v/v acetone/water, using an "EFD Valematic" atomizer (Nolico Co., Hampton Falls, N.H.) operating at about 10 psi (0.67 bar). Coated devices were dried about 15 min. at room temperature, and then rinsed by dipping for about 1 minute into distilled water. After patting with filter paper co remove moisture, the devices were again rinsed in fresh distilled water, patted dry, and vacuum dried overnight. Comparison of coated and uncoated surfaces by contact angle measurement showed a substantial increase in hydrophilicity of the coated device surfaces (decrease in contact angle with water).

Devices, about 10 mm by 19 mm, were rolled on a 0.042 inch (1050 micron) mandrel to obtain a roll about 10 mm long along the mandrel. The roll was secured with Teflon tape and heat set at 50 degrees C at least 12 hours. The rolled devices were cold sterilized with ethylene oxide (room temperature, 18 hours, Anderson system) while placed in standard EtO sterilization bags.

Example 5
Deployment in Animals

Devices of Example 4 were positioned on the balloon of a custom balloon angioplasty catheter, which had an optically transparent guide wire lumen continuing through the balloon region, and secured with a moveable sheath. After insertion of the catheter through the carotid artery of a dog and localization in the iliac artery by standard techniques, the guidewire was removed and replaced with an optical fiber with a 15 mm diffuser tip, which had been calibrated to emit 3 watts of power when powered by a diode laser operating at about 800 nm (Rare Earth Medical). The sheath was then retracted under radiographic observation, and the balloon was inflated at 6 atmospheres to deploy the device. Laser energy was emitted for 45 to 60 seconds, while 6 bar pressure was maintained, to mold the device to the artery wall and to seal it to itself where there was overlap. Pressure was maintained for an additional 5 minutes while the device cooled, and then the balloon was deflated and the catheter was removed, leaving the device as a coating in the artery.

(The times were chosen after a simulation in an excised cow artery kept in a 37 degree bath, in which a thermocouple was positioned between the device and the artery wall. Temperature at the end of 60 seconds of illumination was about 65 degrees, while the material had returned to blood temperature after 5 additional minutes.)

Example 6

Delivery of Therapeutics

Heparin was spray-dried to a fine powder by pumping a 2% w/v solution, in distilled water, through a Lab-Plant™ spray drier at 12 ml/min, 100 degrees C inlet temperature. Final particle size was in the range of 1–10 microns diameter. Six grams of polycaprolactone was dissolved in 60 ml of chloroform. To 20 ml of this solution, spray-dried heparin was added to a final concentration of 5%, 10% and 30% w/w (i.e., 1, 2 and 6 grams). The solutions were homogenized for 7 minutes using a Virtis homogenizer. Films were cast, and 4 layers of film were laminated as in example 4.

Square devices 1 cm by 1 cm were placed in 1.5 ml microcentrifuge tubes containing 1 ml phosphate buffered saline preserved with sodium azide. Samples were incubated at 37 degrees C. Buffer was periodically removed for analysis and replaced with fresh buffer. Heparin content of the buffer was analyzed by the standard Azure B method. Retention of heparin after the first 12 hours was about 70%, 45% and 20% of the amount contained in the 5%, 10% and 30% loadings respectively. Heparin continued to elute slowly over the next 500 hours, at which point about 37%, 20% and 10% respectively was retained in the devices.

Example 7

Rapid Crystallization

The time course of the experiment of Example 5 is too long for use in certain situations, such as human coronary arteries. Devices were made as in Example 6, but containing 0, 1% and 10% of dibenzylidene sorbitol (Millad™ 3905), and then rolled for delivery as in example 4. Devices were tester in a tube simulating an artery. After a standard heating pulse, the minimum time to obtain sufficient strength development to allow detachment of the balloon was 146 seconds, 71 sec., and 39 sec. for 0,1 and 10% Millad nucleator, respectively Equivalents Although specific features of the invention are included in some embodiments and drawings and not others, it should be noted that certain features may be combined with other features in accordance with the invention.

In addition, it should be noted that the invention is not intended to be limited to the specific materials and construction described herein.

It should be understood that the foregoing description of the invention is intended to be merely illustrative thereof, that the illustrative embodiments are presented by way of example only, and that other modifications, embodiments, and equivalents may be apparent to those skilled in the art without departing from its spirit.

Having thus described the invention, what we desire to claim and secure by Letters Patent is:

1. A method for providing a polymeric material on a tissue surface, comprising:
positioning, proximate to a tissue surface, a polymeric article that contains a chromophore having an absorption characteristic;
exposing the polymeric article to electromagnetic radiation in a wavelength range that matches the absorption characteristic of the chromophore for a period of time sufficient to render the article softened; and
reconfiguring the softened article, then applying the reconfigured, softened article to the tissue surface and molding the surface of the article facing the tissue surface into intimate and conforming contact with the tissue surface, the chromophore, polymeric article, and wavelength range of electromagnetic radiation being selected such that the molding is effected under conditions tolerable by the tissue surface.

2. A method as in claim 1, further comprising allowing the polymeric article to harden.

3. A method as in claim 1, wherein the tissue surface comprises an interior surface of a tissue lumen or hollow organ.

4. A method as in claim 3, wherein the tissue surface is a surface of a blood vessel.

5. A method as in claim 1, wherein the polymeric article is made of material from the group consisting of polymers of caprolactones, anhydrides, lactides, glycolides, oxyalkylenes, and combinations thereof.

6. A method as in claim 1, wherein the chromophore comprises a dye or pigment.

7. A method as in claim 1, wherein the polymeric article is biodegradable.

8. A method as in claim 1, wherein the molding step is carried out by urging the polymeric article against the tissue surface with a radially expandable portion of a catheter.

9. A method as in claim 8, wherein the radially expandable portion of the catheter comprises a dilatation balloon.

10. A method as in claim 1, wherein the polymeric article contains a therapeutic agent.

11. A method as in claim 1, wherein the polymeric article comprises a multi-layer structure.

12. A method as in claim 1, wherein the polymeric article contains a biocompatible coating.

13. A method as in claim 1, further comprising:
positioning the polymeric article on an article-forming element positioned at a distal region of a tubular shaft of a catheter, the distal region constructed and arranged for insertion into a patient, the shaft also including a proximal region adapted to remain outside of the patient.

14. A method as in claim 13, wherein the molding step is carried out by expanding the article-forming element.

15. A method as in claim 14, wherein the article-forming element is a radially-expandable dilatation balloon.

16. A method as in claim 13, wherein the step of exposing the polymeric article to electromagnetic radiation comprises activating a source of electromagnetic radiation connected, via an optical fiber, to an emitter located at the distal region of the shaft.

17. A method as in claim 1, wherein the exposing step comprises exposing the polymeric article to the electromagnetic radiation for a period of time sufficient to soften a surface of the article facing the tissue surface.

18. A method as in claim 1, the method involving paving or stabilizing an irregularly contoured tissue surface of a lumen or hollow organ of a mammal.

19. A method for providing a polymeric material on a tissue surface, comprising:
positioning, proximate to a tissue surface, a polymeric article that contains a chromophore having an absorption characteristic;
exposing the polymeric article to electromagnetic radiation in a wavelength range that matches the absorption characteristic of the chromophore and that is of a wavelength range that is not readily absorbed by the tissue surface for a period of time sufficient to soften the article; and molding the surface of the article facing the tissue surface into intimate and conforming contact with the tissue surface, the chromophore, polymeric article, and wavelength range of electromagnetic radiation being selected such that the molding is effected under conditions tolerable by the tissue surface.

20. A method as in claim 19, the method involving paving or stabilizing an irregularly contoured tissue surface of a lumen or hollow organ of a mammal.

21. A method as in claim 19, wherein the polymeric article is made of material from the group consisting of polymers of caprolactones, anhydrides, lactides, glycolides, oxyalkylenes, and combinations thereof.

22. A method as in claim 19, wherein the polymeric article is biodegradable.

23. A method as in claim 19, wherein the molding step is carried out by urging the polymeric article against the tissue surface with a radially expandable portion of a catheter.

24. A method as in claim 19, wherein the polymeric article contains a therapeutic agent.

25. A method for providing a polymeric material on a tissue surface, comprising:

positioning, proximate to a tissue surface, a polymeric article comprising a copolymer of at least two moieties selected from the group consisting of caprolactones, anhydrides, lactides, and glycolides that contains a chromophore having an absorption characteristic;

exposing the polymeric article to electromagnetic radiation in a wavelength range that matches the absorption characteristic of the chromophore for a period of time sufficient to soften the article; and molding the surface of the article facing the tissue surface into intimate and conforming contact with the tissue surface, the chromophore, polymeric article, and wavelength range of electromagnetic radiation being selected such that the molding is effected under conditions tolerable by the tissue surface.

26. A method as in claim 25, the method involving paving or stabilizing an irregularly contoured tissue surface of a lumen or hollow organ of a mammal.

27. A method as in claim 25, wherein the molding step is carried out by urging the polymeric article against the tissue surface with a radially expandable portion of a catheter.

28. A method as in claim 25, wherein the polymeric article contains a therapeutic agent.

29. A method for providing a polymeric material on a tissue surface, comprising:

positioning, proximate to a tissue surface, a polymeric article that contains a chromophore that is a dye or pigment selected from the group consisting of indocyanine, eosin, copper phthalocyanine, and combinations thereof, having an absorption characteristic;

exposing the polymeric article to electromagnetic radiation in a wavelength range that matches the absorption characteristic of the chromophore for a period of time sufficient to soften the article; and molding the surface of the article facing the tissue surface into intimate and conforming contact with the tissue surface, the chromophore, polymeric article, and wavelength range of electromagnetic radiation being selected such that the molding is effected under conditions tolerable by the tissue surface.

30. A method as in claim 29, the method involving paving or stabilizing an irregularly contoured tissue surface of a lumen or hollow organ of a mammal.

31. A method as in claim 29, wherein the polymeric article is made of material from the group consisting of polymers of caprolactones, anhydrides, lactides, glycolides, oxyalkylenes, and combinations thereof.

32. A method as in claim 29, wherein the polymeric article is biodegradable.

33. A method as in claim 29, wherein the molding step is carried out by urging the polymeric article against the tissue surface with a radially expandable portion of a catheter.

34. A method as in claim 29, wherein the polymeric article contains a therapeutic agent.

35. A method for providing a polymeric material on a tissue surface, comprising:

positioning, proximate to a tissue surface, a polymeric article that contains a chromophore having an absorption characteristic;

exposing the polymeric article to electromagnetic radiation in a wavelength range that matches the absorption characteristic of the chromophore for a period of time sufficient to soften the entire article to the point that it becomes fluent; and molding the surface of the article facing the tissue surface into intimate and conforming contact with the tissue surface, the chromophore, polymeric article, and wavelength range of electromagnetic radiation being selected such that the molding is effected under conditions tolerable by the tissue surface.

36. A method as in claim 35, the method involving paving or stabilizing an irregularly contoured tissue surface of a lumen or hollow organ of a mammal.

37. A method as in claim 35, wherein the polymeric article is made of material from the group consisting of polymers of caprolactones, anhydrides, lactides, glycolides, oxyalkylenes, and combinations thereof.

38. A method as in claim 35, wherein the polymeric article is biodegradable.

39. A method as in claim 35, wherein the molding step is carried out by urging the polymeric article against the tissue surface with a radially expandable portion of a catheter.

40. A method as in claim 35, wherein the polymeric article contains a therapeutic agent.

41. A method for providing a polymeric material on a tissue surface, comprising:

positioning, proximate to a tissue surface, a polymeric article that contains a chromophore having an absorption characteristic;

exposing the polymeric article to electromagnetic radiation in a wavelength range that matches the absorption characteristic of the chromophore for a period of time sufficient to soften the entire article to the point that it becomes fluent;

determining when the polymeric article becomes fluent; and molding the surface of the article facing the tissue surface into intimate and conforming contact with the tissue surface, the chromophore, polymeric article, and wavelength range of electromagnetic radiation being selected such that the molding is effected under conditions tolerable by the tissue surface.

42. A method as in claim 41, the method involving paving or stabilizing an irregularly contoured tissue surface of a lumen or hollow organ of a mammal.

43. A method as in claim 41, wherein the polymeric article is made of material from the group consisting of polymers of caprolactones, anhydrides, lactides, glycolides, oxyalkylenes, and combinations thereof.

44. A method as in claim 41, wherein the polymeric article is biodegradable.

45. A method as in claim 41, wherein the molding step is carried out by urging the polymeric article against the tissue surface with a radially expandable portion of a catheter.

46. A method as in claim 41, wherein the polymeric article contains a therapeutic agent.

47. A method for providing a polymeric article on a tissue surface, comprising:

positioning a polymeric article, which contains a chromophore having an absorption characteristic, surrounding an article-forming element proximate to a tissue surface at a distal region of a tubular shaft of a catheter, the distal region constructed and arranged for insertion into a patient, the shaft also including a proximal region adapted to remain outside of the patient;

exposing the polymeric article to electromagnetic radiation in a wavelength range that matches the absorption characteristic of the chromophore for a period of time sufficient to soften the article; and molding the surface of the article facing the tissue surface into intimate and conforming contact with the tissue surface by expanding the article-forming element, the chromophore, polymeric article, and wavelength range of electromagnetic radiation being selected such that the molding is effected under conditions tolerable by the tissue surface.

48. A method as in claim 47, the method involving paving or stabilizing an irregularly contoured tissue surface of a lumen or hollow organ of a mammal.

49. A method as in claim 47, wherein the polymeric article is made of material from the group consisting of polymers of caprolactones, anhydrides, lactides, glycolides, oxyalkylenes, and combinations thereof.

50. A method as in claim 47, wherein the polymeric article is biodegradable.

51. A method as in claim 47, wherein the polymeric article contains a therapeutic agent.

52. A method for providing a polymeric material on a tissue surface, comprising:

positioning, proximate to a tissue surface, a polymeric article that contains a thermochromic chromophore having an absorption characteristic;

exposing the polymeric article to electromagnetic radiation in a wavelength range that matches the absorption characteristic of the chromophore for a period of time sufficient to soften the article; and molding the surface of the article facing the tissue surface into intimate and conforming contact with the tissue surface, the chromophore, polymeric article, and wavelength range of electromagnetic radiation being selected such that the molding is effected under conditions tolerable by the tissue surface.

53. A method as in claim 52, the method involving paving or stabilizing an irregularly contoured tissue surface of a lumen or hollow organ of a mammal.

54. A method as in claim 52, wherein the polymeric article is made of material from the group consisting of polymers of caprolactones, anhydrides, lactides, glycolides, oxyalkylenes, and combinations thereof.

55. A method as in claim 52, wherein the polymeric article is biodegradable.

56. A method as in claim 52, wherein the molding step is carried out by urging the polymeric article against the tissue surface with a radially expandable portion of a catheter.

57. A method as in claim 53, wherein the polymeric article contains a therapeutic agent.

58. A method for providing a polymeric material on a tissue surface, comprising:

positioning, proximate to a tissue surface, a polymeric article that contains a chromophore having an absorption characteristic;

exposing the polymeric article to electromagnetic radiation in a wavelength range in a spectrum of between about 300–1000 nm that matches the absorption characteristic of the chromophore for a period of time sufficient to soften the article; and molding the surface of the article facing the tissue surface into intimate and conforming contact with the tissue surface, the chromophore, polymeric article, and wavelength range of electromagnetic radiation being selected such that the molding is effected under conditions tolerable by the tissue surface.

59. A method as in claim 58, wherein the wavelength range is in a spectrum of between about 500 and 850 nm.

60. A method as in claim 58, the method involving paving or stabilizing an irregularly contoured tissue surface of a lumen or hollow organ of a mammal.

61. A method as in claim 58, wherein the polymeric article is made of material from the group consisting of polymers of caprolactones, anhydrides, lactides, glycolides, oxyalkylenes, and combinations thereof.

62. A method as in claim 58, wherein the polymeric article is biodegradable.

63. A method as in claim 58, wherein the molding step is carried out by urging the polymeric article against the tissue surface with a radially expandable portion of a catheter.

64. A method as in claim 58, wherein the polymeric article contains a therapeutic agent.

* * * * *

UNITED STATES PATENT AND TRADEMARK OFFICE
CERTIFICATE OF CORRECTION

PATENT NO. : 5,849,035
DATED : December 15, 1998
INVENTOR(S) : Chandrashekhar P. Pathak et al.

It is certified that error appears in the above-identified patent and that said Letters Patent is hereby corrected as shown below: In column 30, line 16, please change "53" to --52--.

Signed and Sealed this

Eighteenth Day of May, 1999

Attest:

Q. TODD DICKINSON

*Attesting Officer*     *Acting Commissioner of Patents and Trademarks*